US012778985B2

(12) United States Patent
Gu et al.

(10) Patent No.: US 12,778,985 B2
(45) Date of Patent: Nov. 3, 2026

(54) USE OF MICRONEEDLE PATCH TO PROMOTE HAIR GROWTH

(71) Applicant: North Carolina State University, Raleigh, NC (US)

(72) Inventors: Zhen Gu, Los Angeles, CA (US); Guang Yang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 1150 days.

(21) Appl. No.: 17/047,186

(22) PCT Filed: Apr. 11, 2019

(86) PCT No.: PCT/US2019/026933
§ 371 (c)(1),
(2) Date: Oct. 13, 2020

(87) PCT Pub. No.: WO2019/200063
PCT Pub. Date: Oct. 17, 2019

(65) Prior Publication Data

US 2021/0161968 A1 Jun. 3, 2021

Related U.S. Application Data

(60) Provisional application No. 62/657,423, filed on Apr. 13, 2018.

(51) Int. Cl.
*A61K 35/28* (2015.01)
*A61K 9/00* (2006.01)
(Continued)

(52) U.S. Cl.
CPC ............ *A61K 35/28* (2013.01); *A61K 9/0021* (2013.01); *A61K 9/5031* (2013.01);
(Continued)

(58) Field of Classification Search
CPC .... A61K 35/28; A61K 9/0021; A61K 9/5031; A61K 9/7084; A61K 31/405;
(Continued)

(56) References Cited

U.S. PATENT DOCUMENTS

| | | | | |
|---|---|---|---|---|
| 2011/0195124 | A1 | 8/2011 | Jir | |
| 2012/0276188 | A1* | 11/2012 | Barrows | A61L 27/3834 424/443 |

(Continued)

FOREIGN PATENT DOCUMENTS

| | | | |
|---|---|---|---|
| CN | 1553793 | A | 12/2004 |
| CN | 107530296 | A | 1/2018 |

(Continued)

OTHER PUBLICATIONS

Chan and Wasserman, 1993 "Direct Colorimetric Assay of Free Thiol Groups and Disulfide Bonds in Suspensions of Solubilized and Particulate Cereal Proteins," Cereal Chern. 70, 22-26.

(Continued)

*Primary Examiner* — Bhisma Mehta
*Assistant Examiner* — Fatimata Sahra Diop
(74) *Attorney, Agent, or Firm* — Jenkins, Taylor & Hunt, P.A.

(57) ABSTRACT

Compositions comprising polymeric networks comprising combinations of small molecule hair growth agents and natural products (e.g., vesicles, such as stem cell-derived exosomes) are described. The polymeric network can, for example, comprise keratin crosslinked via intermolecular disulfide bonds. Alternatively, the polymeric network can comprise keratin or a derivative thereof and another cross-linked hydrophilic polymer. Microneedles, microneedle arrays, and skin patches comprising the compositions are
(Continued)

also described, as are methods of treating hair loss and/or promoting hair growth using the microneedles, microneedle arrays and/or skin patches.

22 Claims, 9 Drawing Sheets

(51) Int. Cl.

| | |
|---|---|
| ***A61K 9/50*** | (2006.01) |
| ***A61K 9/70*** | (2006.01) |
| ***A61K 31/405*** | (2006.01) |
| ***A61K 47/42*** | (2017.01) |
| ***A61M 37/00*** | (2006.01) |
| ***A61P 17/14*** | (2006.01) |

(52) U.S. Cl.
CPC .......... *A61K 9/7084* (2013.01); *A61K 31/405* (2013.01); *A61K 47/42* (2013.01); *A61M 37/0015* (2013.01); *A61P 17/14* (2018.01); *A61M 2037/0023* (2013.01); *A61M 2037/0053* (2013.01); *A61M 2037/0061* (2013.01)

(58) Field of Classification Search
CPC .... A61K 47/42; A61K 9/5068; A61K 9/5153; A61K 9/7007; A61K 9/703; A61K 31/19; A61K 31/496; A61K 31/506; A61K 31/565; A61K 31/58; A61K 45/06; A61K 2800/412; A61K 2800/91; A61K 8/0208; A61K 8/042; A61K 8/14; A61K 8/65; A61K 8/735; A61K 8/981; A61K 31/203; A61K 31/7076; A61K 35/36; A61K 38/015; A61K 47/36; A61K 8/492; A61K 8/73; A61K 9/06; A61K 47/20; A61K 47/30; A61K 2300/00; A61K 2800/56; A61M 37/0015; A61M 2037/0023; A61M 2037/0053; A61M 2037/0061; A61P 17/14; A61Q 7/00
See application file for complete search history.

(56) References Cited

U.S. PATENT DOCUMENTS

| | | | | |
|---|---|---|---|---|
| 2013/0209528 A1* | 8/2013 | Levi | A61K 8/981 | 424/520 |
| 2014/0079686 A1* | 3/2014 | Barman | A61B 17/00491 | 424/94.67 |
| 2019/0026933 A1 | 1/2019 | Nam et al. | | |
| 2020/0157093 A1* | 5/2020 | Lowry | A61Q 7/00 | |

FOREIGN PATENT DOCUMENTS

| | | | |
|---|---|---|---|
| EP | 2629782 | A1 | 8/2013 |
| EP | 3768226 | A1 | 1/2021 |
| KR | 20180015994 | A | 2/2018 |
| KR | 1020210003799 | A | 1/2021 |
| WO | WO 2011/084925 | A2 | 7/2011 |
| WO | WO 2016/057833 | A1 | 4/2016 |
| WO | WO 2017/078641 | A1 | 5/2017 |
| WO | WO 2018/039612 | A1 | 3/2018 |

OTHER PUBLICATIONS

Communication of European Publication Application No. 19785580 dated Jan. 13, 2021.

European Search Report corresponding to Application No. 19785580 dated Dec. 9, 2021.

Hsu et al (2011) "Dynamics between Stem Cells, Niche, and Progeny in the Hair Follicle," Cell, 144, 92-105.

International Preliminary Report on Patentability corresponding to U.S Application No. PCT/US2019/26933 dated Oct. 13, 2020.

International Search Report and Written Opinion corresponding to US Application No. PCT/US2019/26933 dated Jun. 28, 2019.

Jiang et al. (2017), "Exosomes Mediate Epithelium-Mesenchyme Crosstalk in Organ Development," ACS Nano, 11, pp. 1-20.

Lolli et al, (2017), "Androgenetic alopecia: a review," Endocrine, 57, pp. 9-17.

Luan et al. (2017), "Engineering exosomes as refined biological nanoplatforms for drug delivery," Acta Pharmacologica Sinica, 38, pp. 754-763.

Moore and Lemischka (2006) "Stem Cells and Their Niches," Science, 311, pp. 1880-1885.

MuEller-RoEver et al., (2001) "A Comprehensive Guide for the Accurate Classification of Murine Hair Follicles in Distinct Hair Cycle Stages," J. Investig. Dermatol., 117 (1), pp. 3-15.

Notification of the Publication of the International Application corresponding to US Application No. PCT/US 2019/26933 dated Oct. 17, 2019.

Office Action Corresponding to Chinese Application No. 2023092800434910 dated Sep. 28, 2023.

Oh et al., (2016) "A Guide to Studying Human Hair Follicle Cycling In Vivo," J. Investig. Dermatol. , 136(1), pp. 34-44.

Pace et al., 2014 "A Human Hair Ketatin Hydrogel Scaffold Enhances Median Nerve Regeneration in Nonhuman Primates: an Electrophysiological and Histological Study," Tissue Engineering vol. 20, pp. 507-517.

Rajendran et al., "Extracellular vesicles derived from MSCs activates dermal papilla cell in vitro and promotes hair follicle conversion from telogen to anagen in mice," Scientific Reports pp. 1-12.

Singh et al., "Thiol-Disulfide Interchange," John Wiley & Sons, Inc., Chichester, United Kingdom, 1993, 6433-658.

Zhang et al. (2015) "HucMSC-Exosome Mediated-Wnt4 Signaling Is Required for Cutaneous Wound Healing," Stem Cells, 33, pp. 2158-2168.

Zhang et al., (2017), "Locally Induced Adipose Tissue Browning by Microneedle Patch for Obesity Treatment," ACS Nano, 11, pp. 1-16.

Aimee F., et al., "Lactate dehydrogenase activity drives hair follicle stem cell activation", Nature Cell Biology, vol. 19, No. 9, Aug. 14, 2017 (Aug. 14, 2017), pp. 1017-1026, XP055467938.

First office action corresponding to Chinese Application No. 201980033756.7 dated Oct. 8, 2022, 17 pages.

First office action corresponding to Korea Application No. 10-2020-7032643 dated Feb. 23, 2024, 8 pages.

Jiang, N., et al., "Exosomes Mediate Epithelium-Mesenchyme Crosstalk in Organ Development", vol. 11, No. 8, Aug. 22, 2017, pp. 7736-7746.

Lahiji S.F., et a., "Transcutaneous implantation of valproic acid-encapsulated dissolving microneedles induces hair regrowth", Biomaterials, Elsevier, Amsterdam, NL, vol. 167, Mar. 13, 2018 (Mar. 13, 2018), pp. 69-79, XP085374758.

Notice of Allowance corresponding to Korea Application No. 10-2020-7032643 dated Nov. 18, 2024, 7 pages.

Second office action corresponding to Chinese Application No. 201980033756.7 dated Apr. 20, 2023, 14 pages.

Sovak M., et al., "Fluridil, a Rationally Designed Topical Agent for Androgenetic Alopecia: First clinical Experience", Dermatol Surg, vol. 28, No. 8, Aug. 2002, pp. 678-685.

Yang G., et al., "A Therapeutic Microneedle Patch Made from Hair-Derived Keratin for Promoting Hair Regrowth", Acs Nano, vol. 13, No. 4, Apr. 3, 2019 (Apr. 3, 2019), pp. 4354-4360, XP055867150.

Yang, G., et al., "Comparative study of kerateine and keratose based composite nanofibers for biomedical applications", Materials Science & Engineering C, vol. 83, 2018, pp. 1-8.

Communication pursuant to Article 94(3) EPC of European Publication Application No. 19785580 dated Feb. 20, 2025, pp. 6.

* cited by examiner

USE OF MICRONEEDLE PATCH TO PROMOTE HAIR GROWTH

RELATED APPLICATIONS

This application claims priority to and the benefit of U.S. Provisional Patent Application Ser. No. 62/657,423, filed Apr. 13, 2018; the disclosure of which is incorporated herein by reference in its entirety.

TECHNICAL FIELD

The presently disclosed subject matter relates to compositions for the delivery of combinations of natural products (e.g., extracellular vesicles or stem cells) and small molecule hair growth agents. The composition can comprise a keratin hydrogel or a polymeric network comprising keratin or a derivative thereof and a crosslinked hydrophilic polymer other than keratin. The presently disclosed subject matter also relates to microneedles, microneedle arrays, and skin patches comprising the composition: to methods of preparing the microneedle arrays; and to methods of treating hair loss and/or promoting hair growth using the microneedles, arrays, or skin patches.

Abbreviations

° C.=degrees Celsius
%=percentage
μg=microgram
μl=microliter
μm=micrometer or micron
μmol=micromole
BSA=bovine serum albumin
cm=centimeter
DCM=dichloromethane
DiD=1,1'-dioxtadecyl-3,3,3',3'-tetramethyl-indodicarbocyanine 4-chlorobenzenesulfonate
DiI=1,1'-Dioctadecyl-3,3,3',3'-tetramethyl-indocarbacyanine perchlorate
DLS=dynamic light scattering
EV=extracellular vesicle
FBS=fetal bovine serum
FITC=fluorescein isothiocyante
FTIR=Fourier-transform infrared spectroscopy
g=gram
h=hour
HA=hyaluronic acid
HFSCs=hair follicle stem cells
HMN=hydrogel microneedle patch
HPLC=high performance liquid chromatography
kDa=kilodalton
MBA=N,N'-methylene bisacrylamide
mg=milligram
m-HA=acrylate-modified hyaluronic acid
min=minutes
ml=milliliter
mm=millimeter
MN=microneedle
MTT=3(4,5-dimethylthiazol-2-yl)-2,5-diphenyltetrazolium bromide
NP=nanoparticle
MSC=mesenchymal stem cell
Mw=weight-average molecular weight
MWCO=molecular weight cutoff
N=Newton
nm=nanometer
PBS=phosphate buffered saline
PEG=poly(ethylene glycol)
PLGA=poly(lactic acid-co-glycolic acid)
PVA=polyvinyl alcohol
RhB=rhodamine B
s.c.=subcutaneous
SDS=sodium dodecyl sulfate
SEM=scanning electron microscope
s.d.=standard deviation
TEM=transmission electron microscope
UK5099=2-cyano-3-(1-phenyl-1H-indol-3-yl)-2-propenoic acid
UV=ultraviolet
wt %=weight percent

BACKGROUND

More than 50% of the general population suffers from hair loss or alopecia. The most common strategies for hair loss treatment include drug therapy, e.g., topical treatment with minoxidil or orally administered finasteride. See Chueh et al. (2013) Expert Opin. Biol. Ther., 13(3), 377-391; and Lolli et al., (2017) Endocrine, 57, 9-17. However, these treatments generally offer only short-term improvement. To have continued benefit, treatment with these drugs involves their continued use, which can lead to adverse side effects. Autologous hair transplantation can be a reliable alternative option; however, it involves an invasive surgical operation and is limited to cases where autologous hair follicles are abundant. See Chueh et al. (2013) Expert Opin. Biol. Ther., 13(3), 377-391; and Lolli et al., (2017) Endocrine, 57, 9-17.

Accordingly, there is an ongoing need for additional treatment options for preventing hair loss and/or promoting hair growth. In particular, there is a need for treatments that are effective in promoting local hair growth, that provide sustained delivery of therapeutic agents and/or sustained therapeutic results, and that are non-painful and have reduced side effects.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a composition comprising: (a) a hydrophilic polymer network comprising keratin or a derivative thereof; (b) a natural product selected from the group comprising vesicles, stem cells, and vesicle-derived molecules, optionally wherein the vesicles are exosomes, further optionally wherein the natural product comprises mesenchymal stem cell (MSC)-derived exosomes; and (c) a small molecule hair growth agent.

In some embodiments, the hydrophilic polymer network comprises a keratin hydrogel. In some embodiments, the keratin hydrogel is crosslinked via intermolecular disulfide bonds. In some embodiments, the keratin hydrogel is a hydrogel prepared from an aqueous solution comprising between about 5 weight % (wt %) and about 20 wt % keratin and between about 0.1 wt % and about 1 wt % cysteine, optionally about 8 weight % keratin and/or about 0.4 wt % cysteine.

In some embodiments, the hydrophilic polymer network comprises: (i) a crosslinked hydrophilic polymer wherein the crosslinked hydrophilic polymer is other than keratin, optionally wherein the crosslinked hydrophilic polymer is selected from the group comprising methacrylated hyaluronic acid (m-HA) or another glucosaminoglycan or copolymer or derivative thereof; polyvinyl alcohol (PVA) or a copolymer or derivative thereof; a polysaccharide; a poly(amino acid), a protein other than keratin; polyvinyl pyrrolidone (PVP); a poly(alkylene glycol) or a poly(alkylene oxide); poly(hydroxyalkyl methacrylamide), a polyhydroxy acid; combinations thereof, and copolymers thereof; and (ii) keratin or a derivative thereof.

In some embodiments, the small molecule hair growth agent comprises one or more selected from the group comprising 2-cyano-3-(1-phenyl-1H-indol-3-yl)-2-propenoic acid (UK5099), minoxidil, finasteride, valproic acid, cortexolone 17α, 17α-estradiol, adenosine, all trans retinoic acid, fluridil, RU-58841, suberohydroxamic acid (4-methoxycarbonyl) phenyl ester, and ketoconazole. In some embodiments, the small molecule hair growth agent is encapsulated in a nanoparticle comprising a biodegradable polymer. In some embodiments, the biodegradable polymer is polylactic-co-glycolic acid (PLGA).

In some embodiments, the composition comprises between about 0.01 milligrams (mg) and about 2 mg exosomes, optionally MSC-derived exosomes. In some embodiments, the composition comprises between about 0.05 micrograms (μg) and about 1 mg of the small molecule hair growth agent.

In some embodiments, the presently disclosed subject matter provides a microneedle comprising a composition comprising: (a) a hydrophilic polymer network comprising keratin or a derivative thereof; (b) a natural product selected from the group comprising vesicles, stem cells, and vesicle-derived molecules, optionally wherein the vesicles are exosomes, further optionally wherein the natural product comprises mesenchymal stem cell (MSC)-derived exosomes; and (c) a small molecule hair growth agent.

In some embodiments, the presently disclosed subject matter provides a microneedle array comprising a plurality of microneedles comprising a composition comprising: (a) a hydrophilic polymer network comprising keratin or a derivative thereof; (b) a natural product selected from the group consisting of vesicles, stem cells, and vesicle-derived molecules, optionally wherein the vesicles are exosomes, further optionally wherein the natural product comprises mesenchymal stem cell (MSC)-derived exosomes; and (c) a small molecule hair growth agent; optionally wherein each of said plurality of microneedles has a length of between about 400 and about 1000 micrometers, further optionally wherein each of the plurality of microneedles has a length of about 600 micrometers and/or a base diameter of about 300 micrometers. In some embodiments, the presently disclosed subject matter provides a skin patch comprising the microneedle array, optionally wherein said patch comprises a protective backing layer, a removable backing layer, or a backing layer comprising a skin compatible adhesive.

In some embodiments, the presently disclosed subject matter provides a method of treating hair loss and/or promoting hair growth in a subject in need thereof, wherein the method comprises administering a microneedle array as disclosed herein or a skin patch as disclosed herein to the subject, wherein the administering comprises contacting the array or skin patch with a skin surface of the subject, wherein the skin surface comprises one or more hair follicles. In some embodiments, the contacting comprises contacting the skin surface of the subject with the array or patch daily, optionally wherein the daily contacting is for between about one and about 24 hours per day. In some embodiments, the subject is a human.

In some embodiments, the presently disclosed subject matter provides a method of preparing a microneedle array comprising a plurality of microneedles comprising a composition comprising a hydrophilic polymer network comprising keratin or a derivative thereof; a natural product selected from the group consisting of vesicles, stem cells, and vesicle-derived molecules, optionally wherein the vesicles are exosomes, further optionally wherein the natural product comprises mesenchymal stem cell (MSC)-derived exosomes; and a small molecule hair growth agent, wherein the method comprises: (a) providing a mold comprising one or more microcavities, optionally wherein each of the one or more microcavities is approximately conical in shape and/or wherein the microcavities have a depth of between about 400 and about 1000 micrometers; (b) filling at least a portion of the one or more microcavities of the mold with a first aqueous solution comprising: (i) keratin, (ii) a natural product selected from vesicles, stem cells, and vesicle-derived molecules, optionally wherein the vesicles are exosomes, further optionally wherein the natural product comprises mesenchymal stem cell (MSC)-derived exosomes; (iii) a small molecule hair growth therapeutic agent, and (iv) cysteine, optionally wherein the molecule hair loss therapeutic agent is embedded in a biodegradable polymer nanoparticle, further optionally wherein the small molecule hair growth therapeutic agent is UK5099; (c) placing the mold under air or oxygen for a period of time to form a keratin hydrogel; (d) dropping a second aqueous solution onto the mold, wherein said second aqueous solution comprises a hydrophilic polymer; (e) drying the mold for an additional period of time; and (f) removing the microarray from the mold.

In some embodiments, the first aqueous solution comprises between about 5 weight % (wt %) and about 20 wt % keratin and between about 0.1 wt % cysteine and about 1.0 wt % cysteine. In some embodiments, the second aqueous solution comprises hyaluronic acid. In some embodiments, steps (b) and (c) are repeated one or more times.

Accordingly, it is an object of the presently disclosed subject matter to provide compositions and devices for the delivery of combinations of agents to treat hair loss and/or promote hair growth, as well as methods of preparing and using said compositions and devices.

An object of the presently disclosed subject matter having been stated hereinabove, and which is achieved in whole or in part by the presently disclosed subject matter, other objects will become evident as the description proceeds when taken in connection with the accompanying drawings and examples as best described herein below.

DETAILED DESCRIPTION

Figure 1A:
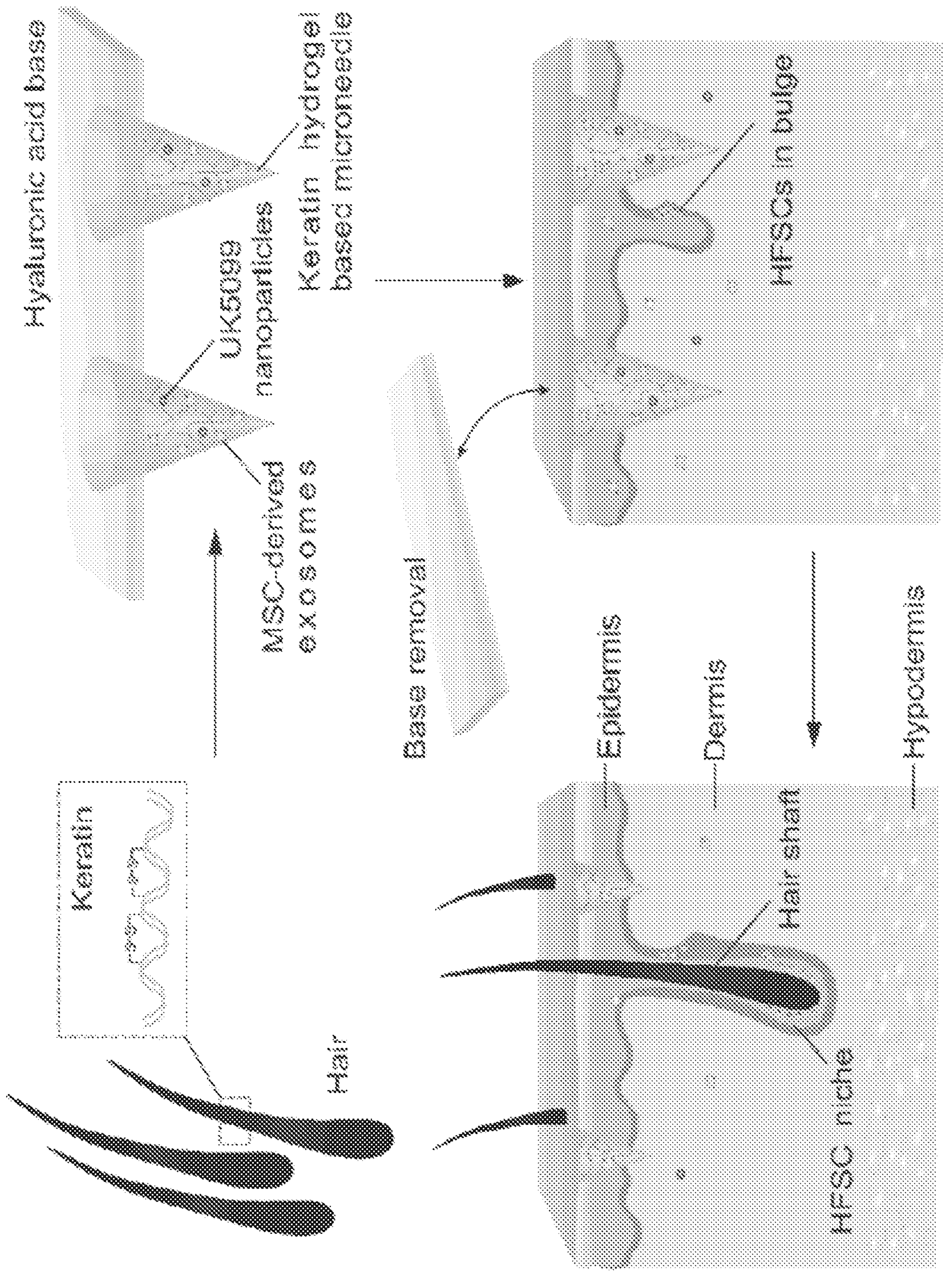
FIG. 1A is a schematic drawing showing a system for hair loss therapy using an exemplary microneedle patch of the presently disclosed subject matter. In the upper left corner is a drawing showing strands of hair containing keratin, which can be used to form the polymeric matrix of the microneedles. As shown in the inset, keratin is a hair-derived protein with a high content of intramolecular disulfide bonds. In the upper right is shown a schematic drawing of a portion of a microneedle skin patch where the microneedles are loaded with mesenchymal stem cell (MSC)-derived exosomes and polymeric nanoparticles comprising 2-cyano-3-(1-phenyl-1H-indol-3-yl)-2-propenoic acid (UK5099), a small molecule hair follicle stem cell activator. The microneedles are attached to a base layer comprising hyaluronic acid. In the lower right, the patch is shown applied to the skin, where the drug-loaded microneedles can penetrate bulges comprising hair follicle stem cells (HFSCs) and release the MSC-derived exosomes and the UK5099. If desired, the hyaluronic base layer can be removed after the patch is applied to the skin, leaving behind the microneedles, which can act as depots for the sustained release of therapeutics. In the lower left corner is a schematic drawing of a cross-section of the skin after the microneedles have been present for a period of time and a new hair is growing the hair shaft where the HFSCs were present. The microneedles have shrunk in size as the result of biodegradation.

The presently disclosed subject matter will now be described more fully hereinafter with reference to the accompanying Figures and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "an agent" or "a polymer" includes a plurality of such agents or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or 10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The terms "nanoscale," "nanomaterial," "nanometer-scale polymer" "nanoparticle", and other grammatical variations thereof refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is less than about 10 nm.

In some embodiments, the nanoparticle is approximately spherical. When the nanoparticle is approximately spherical, the characteristic dimension can correspond to the diameter of the sphere. In addition to spherical shapes, the nanoparticle or other nanoscale material can be disc-shaped, oblong, polyhedral, rod-shaped, cubic, or irregularly-shaped. A nanoscale material can also comprise clusters of sphere-, oblong-, polyhedral-, rod-, disc-, cube- or irregularly-shaped particles or combinations of different shaped particles.

The term "diameter" is art-recognized and is used herein to refer to either the physical diameter or the hydrodynamic diameter. The diameter of an essentially spherical particle can refer to the physical or hydrodynamic diameter. As used herein, the diameter of a non-spherical particle can refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering. In some embodiments, the term "diameter" can also be used to refer to the diameter of a circular cross-section of a physical object, such as a microneedle.

The term "microneedle" as used herein refers to a needle-like structure having at least one region (e.g., length, base diameter, etc.) with a dimension of less than about 1,000 microns (μm). In some embodiments, the term "microneedle" refers to a structure having a dimension between about 1 micron and about 1,000 microns (e.g., about 1, 5, 10, 25, 50, 75, 100, 200, 300, 400, 500, 600, 700, 800, 900 or about 1,000 microns). A microneedle can have a conical or pyramidal shape or can be substantially rod-shaped but comprise one end/tip comprising a conical- or pyramidal-shaped structure.

As used herein, a "macromolecule" refers to a molecule of high relative molecular mass, the structure of which comprises the multiple repetition of units derived from molecules of low relative molecular mass, e.g., monomers and/or oligomers.

An "oligomer" refers to a molecule of intermediate relative molecular mass, the structure of which comprises a small plurality (e.g., 2, 3, 4, 5, 6, 7, 8, 9, or 10) of repetitive units derived from molecules of lower relative molecular mass.

As used herein, a "monomer" refers to a molecule that can undergo polymerization, thereby contributing constitutional units, i.e., an atom or group of atoms, to the essential structure of a macromolecule.

The terms "polymer" and "polymeric" refer to chemical structures that have repeating constitutional units (i.e., multiple copies of a given chemical substructure or "monomer unit"). As used herein, polymers can refer to groups having more than 10 repeating units and/or to groups wherein the repeating unit is other than methylene. Polymers can be formed from polymerizable monomers. A polymerizable monomer is a molecule that comprises one or more reactive moieties {e.g., siloxy ethers, hydroxyls, amines, vinylic groups (i.e., carbon-carbon double bonds), halides (i.e., Cl, Br, F, and I), carboxylic acids, esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as esters or amides, such that they can degrade overtime under biological conditions (e.g., at a certain pH present in vivo or in the presence of enzymes).

A "copolymer" refers to a polymer derived from more than one species of monomer. Each species of monomer provides a different species of monomer unit.

Polydispersity (PDI) refers to the ratio ($M_w/M_n$) of a polymer sample. $M_w$ refers to the mass average molar mass (also commonly referred to as weight average molecular weight). $M_n$ refers number average molar mass (also commonly referred to as number average molecular weight).

"Biocompatible" as used herein, generally refers to a material and any metabolites or degradation products thereof that are generally non-toxic to the recipient (e.g., an animal, such as a human or other mammal) and do not cause any significant adverse effects to the recipient.

"Biodegradable" as used herein, generally refers to a material that will degrade or erode under physiologic conditions to smaller units or chemical species that are capable of being metabolized, eliminated, or excreted by the subject. In some embodiments, the degradation time is a function of polymer composition and morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks.

The term "hydrophilic" can refer to a group that dissolves or preferentially dissolves in water and/or aqueous solutions.

The term "hydrophobic" refers to groups that do not significantly dissolve in water and/or aqueous solutions and/or which preferentially dissolve in fats and/or non-aqueous solutions.

The terms "cross-linking reagent" or "cross-linking agent" as used herein refer to a compound that includes at least two reactive functional groups (or groups that can be deblocked or deprotected to provide reactive functional groups), which can be the same or different. In some embodiments, the two reactive functional groups can have different chemical reactivity (e.g., the two reactive functional groups are reactive (e.g., form bonds, such as covalent bonds) with different types of functional groups on other molecules, or one of the two reactive functional groups tends to react more quickly with a particular functional group on another molecule than the other reactive functional group). Thus, the cross-linking reagent can be used to link (e.g., covalently bond) two other entities (e.g., molecules, polymers, proteins, nucleic acids, vesicles, liposomes, nanoparticles, microparticles, etc.) or to link two groups on the same entity (e.g., a polymer) to form a cross-linked composition.

The term "crosslinked polymer" as used herein refers to a polymer comprising at least one and typically more than one additional bond formed between sites on an individual polymer chain and/or between individual polymer chains. In some embodiments, the sites are bonded to one another via a linker group formed when a crosslinking agent bonds to two different sites on a polymer chain or to sites on two different polymer chains. In some embodiments, the sites are bonded to one another via bonding between a group on one polymer chain and a group on different polymer chain.

The term "embedded" as used herein refers to the entrapment of one entity (e.g., a small molecule therapeutic agent) in another entity (e.g., a polymer network, a nanoparticle, a microparticle, a microneedle, etc.). Generally, "embedded" refers to a non-covalent physical encapsulation of one entity in another, e.g., in the pores or cavities within a polymeric network or polymeric nanoparticle.

The term "small molecule" as used herein refers to a compound having a molecular weight of less than about 900 daltons (e.g., less than about 900 daltons, less than about 850 daltons, less than about 800 daltons, less than about 750 daltons, less than about 700 daltons, less than about 650 daltons, or less than about 600 daltons). Typically, the small molecules of the presently disclosed subject matter comprise synthetic small molecules.

The term "natural product" as used herein refers to a cell, a vesicle, a molecule (e.g., a peptide, protein, lipid, nucleic acid, etc.) or a mixture of molecules derived from a biological organism, tissue, cell, or fluid (e.g., plasma, cell culture medium, etc.). In some embodiments, the natural product comprises an exosome, a stem cell, or an exosome-derived molecule. In some embodiments, the natural product comprises an exosome, an exosomes-containing stem cell culture medium, or an exosome-derived molecule (e.g., an exosome-derived lipid, protein, peptide, or nucleic acid).

II. General Considerations

Mammalian hair can undergo cyclical rounds of resting (telogen), regeneration (anagen), and regression (catagen), which depend on the ability of the hair follicle stem cells (HFSC) to maintain this cycle. See Hsu et al. (2011) Cell, 144, 92-105. HFSCs are normally in telogen, but they can be activated by signals coming from the microenvironment within the hair follicle, or the macroenvironment outside the hair follicle, to enter the anogen phase of a new hair growth cycle. See Moore and Lemischka (2006) Science, 311, 1880-1885; and Hsu et al. (2014) Nature Medicine, 20, 847-857. Generally, the length of hair depends on the duration that HFSC-derived progenitors stay in the anogen phase. In some cases, the HFSCs fail to be activated, which causes an alteration in hair cycle dynamics: telogen phase duration increases while the anagen phase gradually decreases, with the outcome of shorter hair, and eventually bald appearance. See Chueh et al. (2013) Expert Opin. Biol. Ther., 13(3), 377-391.

Exosomes are a type of extracellular vesicle with a nano-spherical membrane-type structure 10-100 nanometers (nm) in diameter and are secreted by many cells and tissues. Exosomes contain various proteins, lipids, and nucleic acids, which are important in cell-to-cell communication. See Luan et al. (2017) Acta Pharmacologica Sinica, 38, 754-763. Studies have indicated that exosomes are associated with many biological processes and some common diseases. See Zhang et al. (2015) Stem Cells, 33, 2158-2168; and Jiang et al. (2017) ACS Nano, 11, 7736-7746.

Further, an exosome is an example of a vesicle, and in particular an example of an extracellular vesicle. By "vesicle" is meant any spherical or semispherical molecule that comprises a lipid membrane and is capable of fusing with other cells and other lipid membranes. The membrane can include proteins and cholesterols, which assist with cell fusion. The vesicle can contain substances such as nucleic acids, proteins, and chemicals. Thus, as used herein, the presently disclosed subject matter comprises vesicles, such as but not limited to exosomes (about 10 nm to about 100 nm in diameter), microvesicles (about 100 nm to about 300 nm in diameter), and apoptotic bodies (about 300 nm to about 500 nm in diameter).

The presently disclosed subject matter relates, in some embodiments, to a composition comprising a combination of a natural product for treating hair loss and/or promoting hair growth and a synthetic small molecule therapeutic agent, such as a therapeutic agent known in the art for treating hair loss and/or promoting hair growth. In some embodiments, the natural product is a vesicle, such as an exosome (e.g., a stem cell-derived exosome) or other extracellular vesicle; a vesicle-derived molecule, such as an exosome-derived protein or nucleic acid; a stem cell; or an exosomes-containing stem cell culture medium. For example, the natural product can be an exosome derived from a stem cell or a stem-cell conditioned medium. In some embodiments, the exosome is an exosome isolated from mesenchymal stem cells (MSCs) or MSC-conditioned medium. The MSC can be derived from skin, bone marrow, gingiva, or another tissue. The exosomes (or other vesicles) can also be derived from tissue cells, such as, but not limited to, human adipose tissue. In some embodiments, the vesicle is replaced by a stem cell from one or more tissues or by one or more molecules derived from a vesicle (e.g., an exosome), such as, but not limited to proteins, such as a cytosolic protein found in the cytoskeleton, an intracellular membrane fusion and/or transport protein, a signal transduction protein, a metabolic enzyme, or a tetraspanin; and nucleic acids, e.g., an exosome-derived messenger RNA (mRNA) and/or microRNA, such as an nucleic acid that can have activity with regard to HFSC activation.

In some embodiments, the combination comprises MSC-derived exosomes and UK5099 or another small molecule therapeutic agent (e.g., a synthetic molecule with a molecular weight of below about 500). In some embodiments, the small molecule therapeutic agent (e.g., the UK5099) can be encapsulated in a biodegradable polymeric nanoparticle (e.g., a PLGA nanoparticle). The use of the nanoparticle can render the small molecule agent more compatible with hydrophilic compositions.

In some embodiments, the small molecule therapeutic agent can be an agent that activates HFSCs. In some embodiments, the small molecule therapeutic agent is an agent that alters glycolytic metabolism by increasing the production of lactate in HFSCs and accelerates hair growth. In some embodiments, the small molecule therapeutic agent is UK5099 (i.e., 2-cyano-3-(1-phenyl-1H-indol-3-yl)-2-propenoic acid) or a therapeutically active derivative or pharmaceutically acceptable salt thereof. In some embodiments, the UK5099 can be replaced by another molecule with potential treatment effect for hair loss including, but not limited to, valproic acid, cortexolone 17α, 17α-estradiol, adenosine, all-trans retinoic acid, fluridil, RU-58841 (also known as PSK-3841 or HMR-3841), suberohydroxamic acid (4-methoxycarbonyl) phenyl ester, ketoconazole, or another small molecule that can adjust the HFSCs signaling pathways, such as, but not limited to, Wnt/β-catenin, bone morphogenic protein (BMP), Notch, and the like, to regulate hair cycling.

In some embodiments, the composition further includes one or more polymeric materials (e.g., a natural or synthetic polymeric material, or a combination thereof) that can form a crosslinked network comprising the exosome and small molecule agent. In some embodiments, the composition is suitable for use in the preparation of microneedle arrays that can be prepared in a skin patch form for use as a convenient and painless transdermal device for sustained delivery of the combination of therapeutic agents to hair follicles.

In some embodiments, the MN array can be used to treat hair loss and/or promote hair growth in a mammalian subject, e.g., a human subject. Accordingly, the MN arrays can be used to treat subjects suffering from hair loss, hair thinning and/or baldness. In some embodiments, the hair loss, hair thinning and/or baldness is the result of male or female pattern baldness. Thus, in some embodiments, the hair loss, hair thinning and/or baldness is the result of genetic factors, age, and/or hormones. In some embodiments, the hair loss, hair thinning and/or baldness can be the result of stress, physical trauma, chronic illness (e.g., an autoimmune disorder, such as alopecia), use of certain medications (e.g., some antidepressants, cytotoxic chemotherapy agents, etc.), ingestion of a poison, or diet (e.g., an iron imbalance, lack of zinc, L-lysine, vitamin B6 or B12, or excessive vitamin A). In some embodiments, the hair loss, hair thinning, and/or baldness can be the result of alopecia, such as, but not limited to, juvenile alopecia, premature alopecia, senile alopecia, alopecia areata, androgenic alopecia, mechanical alopecia, postpartum alopecia, and symptomatic alopecia.

The terms "treat hair loss" and "promote hair growth" include causing a decrease in the rate of hair strand loss or breakage and/or a decrease in the rate of growth of a bald patch or a decrease in the rate of recession of the hair line. Additionally or alternatively, these terms can relate to promoting hair growth in a bald spot, an improvement in hair root sheath thickness, an improvement in hair anchorage, an increase in hair strength, an increase in hair growth rate and/or length, an increase in the number of visible hair strands, and/or an increase in hair volume.

In some embodiments, the presently disclosed subject matter provides a composition comprising: (a) a hydrophilic polymer network; (b) a natural product selected from the group consisting of vesicles (such as exosomes), stem cells and vesicle-derived molecules; and (c) a small molecule hair growth agent. In some embodiments, the hydrophilic polymer network comprises keratin or a derivative thereof. In some embodiments, the natural product comprises exosomes. In some embodiment, the natural product comprises mesenchymal stem cell (MSC)-derived exosomes. In some embodiments, the small molecule hair growth agent is embedded in a nanoparticle comprising a biodegradable polymer.

In some embodiments, the hydrophilic polymer network comprises a keratin hydrogel. The keratin hydrogel can be prepared from an aqueous solution comprising up to about 20 wt % keratin. In some embodiments, the keratin hydrogel is prepared from an aqueous solution that comprises between about 15 wt % keratin and about 20 wt % keratin. In some embodiments, the hydrophilic polymer network comprises or consists of a keratin hydrogel comprising intermolecular disulfide bonds between keratin molecules. In some embodiments, the keratin hydrogel comprising intermolecular disulfide bonds is prepared from an aqueous solution that comprises between about 5 wt % and about 20 wt % keratin (e.g., about 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or about 20 wt % keratin). In some embodiments, the keratin hydrogel is prepared from a solution that comprises between about 7 wt % and about 9 wt % keratin. In some embodiments, the hydrogel is prepared from a solution that comprises about 8 wt % keratin. In some embodiments, the keratin hydrogel is prepared from an aqueous keratin solution that further comprises cysteine. In some embodiments, the keratin hydrogel is prepared from a solution that comprises at least about 0.1 wt % cysteine to up to about 1 wt % cysteine. In some embodiments, the solution comprises between about 0.25 and about 0.75 wt % cysteine (e.g., about 0.25, 0.30, 0.35, 0.40, 0.45, 0.50, 0.55, 0.60, 0.65, 0.70, or about 0.75 wt % cysteine). In some embodiments, the solution comprises between about 0.4 wt % cysteine.

In some embodiments, the hydrophilic polymer network comprises (i) a crosslinked hydrophilic polymeric network of a polymer other than keratin and (ii) keratin or a derivative thereof. Thus, in some embodiments, the polymer network comprises a crosslinked polymer network of a polymer other than keratin comprising keratin or a derivative thereof embedded therein. The non-keratin hydrophilic polymer of the crosslinked hydrophilic polymer network can be a natural polymer or a synthetic polymer. In some embodiments, the crosslinkable hydrophilic polymer is selected from the group including, but not limited to, hyaluronic acid (HA) or a derivative or copolymer thereof; polyvinyl alcohol (PVA) or a copolymer or derivative thereof; a polysaccharide, optionally cellulose or a derivative thereof, chitosan, or dextrin; a poly(amino acid), such as poly-L-serine or poly-L-lysine; a protein other than keratin, e.g., gelatin, collagen, elastin, silk fibroin, spider silk protein, etc.; polyvinyl pyrrolidone (PVP); a poly(alkylene glycol) or a poly(alkylene oxide), optionally a poly(ethylene glycol) (PEG), poly(propylene glycol) (PPG), or poly(ethylene oxide) (PEO); poly(hydroxyalkyl methacrylamide); a polyhydroxy acid, such as poly(lactic acid or a poly(lactic acid-co-glycolic acid) (PGLA); as well as combinations and copolymers thereof. In some embodiments, the hydrophilic polymer is biodegradable. In some embodiments, the hydrophilic polymer is methacrylated HA (m-HA).

The keratin can be extracted from a natural source, including human or other animal skin or a skin appurtenance, such as human hair, wool, or a feather. In some embodiments, the keratin is artificially synthesized, such as via peptide synthesis or by a genetically engineered microorganism or cell. The keratin can be extracted by any suitable method, such as by a chemical method (e.g., reduction, oxidation and/or hydrolysis) or by a physical method, especially when extracted from a natural source. In some embodiments, the composition comprises a derivative of keratin, such as a polypeptide or other segment derived from keratin, chemically modified keratin, or a chemically modified polypeptide or other segment derived from keratin.

When the hydrophilic polymer network comprises a crosslinked hydrophilic polymer other than keratin, the mass ratio of hydrophilic polymer to keratin or keratin derivative can be adjusted as desired. In some embodiments, the ratio of polymer (e.g., m-HA) to keratin can be between about 9/1 and about 1/9. In some embodiments, the composition comprises a ratio of m-HA to keratin of about 2/1.

In some embodiments, the small molecule hair growth agent comprises UK5099 and/or another agent known in the art for use in treating hair loss, hair thinning and or baldness, e.g., minoxidil or finasteride. In some embodiments, the small molecule hair growth agent comprises an agent that alters glycolytic metabolism in stem cells e.g., hair follicle stem cells. In some embodiments, the agent comprises or consists of UK5099.

As noted above, in some embodiments, the small molecule hair growth agent can be provided in nanoparticle form, i.e., embedded in nanoparticle, such as, but not limited to a polymer nanoparticle. In some embodiments, the nanoparticle comprises a biodegradable polymer, such as a polyester or a polyamide. In some embodiments, the biodegradable polymer is selected from the group including, but not limited to, HA, polylactide, polyglycolide, chitosan, polyhydroxy butyrate and combinations or copolymers thereof. In some embodiments, the biodegradable polymer is polylactic-co-glycolic acid (PLGA).

The amount of vesicles (e.g., exosomes) or other natural product and/or the amount of small molecule therapeutic (e.g., UK5099) can vary, e.g., depending upon the size of the microneedle array patch prepared from the composition. As an example, for a microneedle patch comprising a 15×15 needle array, wherein each array has an approximately 300 μm base diameter and a height of about 600 μm, the added amount of vesicles (e.g., exosomes) can be between about 0.01 milligram (mg) and about 2 mg. The amount of small molecule hair growth agent (e.g., UK5099) can be between about 0.05 microgram (μg) and about 1 mg (e.g., about 0.05, 0.1, 0.5, 1.0, 5.0, 10, 50, 100, 200, 300, 400, 500, 600, 700, 800, 900, or about 1000 μg). These amounts can be increased when a larger patch is prepared.

The rate of release of the active components in the presently disclosed composition (i.e., the natural product and the small molecule hair growth agent) can be adjusted by varying the polymer composition, the level of crosslinking of the polymer and/or the level of active agent loading in the crosslinked polymer network.

In some embodiments, the presently disclosed subject matter provides a microneedle comprising a composition as disclosed herein. In some embodiments, the presently disclosed subject matter provides a microneedle array comprising a plurality of such microneedles. For example, in some embodiments, the presently disclosed subject matter provides a microneedle array comprising a plurality of microneedles comprising a crosslinked hydrophilic polymer or polymers, keratin, vesicles, such as exosomes (e.g., MSC-derived exosomes), and a small molecule hair growth agent (e.g., UK5099). In some embodiments, the microneedle array can comprise a plurality of microneedles wherein each of said plurality of microneedles has a length of between about 20 and about 1000 microns (e.g., about 20, 50, 100, 150, 200, 250, 300, 350, 400, 450, 500, 550, 600, 650, 700, 750, 800, 850, 900, 950, or about 1000 microns). In some embodiments, each of the plurality of microneedles has a length of between about 400 microns and about 1000 microns. In some embodiments, each of the plurality of microneedles has a length of at least about 500, 550, 600, 650, 700, 750, or 800 microns. In some embodiments, each of the plurality of microneedles has a length of about 600 microns.

In some embodiments, each microneedle can have an approximately conical or pyramidal shape. In some embodiments, the base of each microneedle can be between about 10 and about 600 microns (e.g., about 20, 50, 75, 100, 150, 200, 250, 300, 350, 400, 450, 500, 550, or about 600 microns) in diameter. In some embodiments, the diameter of each microneedle base can be between about 200 and about 400 microns (e.g., 200, 225, 250, 275, 300, 325, 350, 375, or 400 microns). In some embodiments, the diameter of each microneedle base can be about 300 microns.

In some embodiments, the tip of the microneedles can be less than about 100 microns, less than about 75 microns, less than about 50 microns, less than about 40 microns, less than about 30 microns, or less than about 20 microns. In some embodiments, the tip of each of the microneedles can be about 10 microns.

The microneedle array can comprise a plurality of microneedles, wherein the bases of microneedles are arranged in any suitable two-dimensional pattern. The microneedles can be arranged in a regular array (e.g., a square, rectangular, circular, oval or other shaped pattern) wherein the distance between individual microneedles remains the same or varies in a repeating fashion, or in an irregular array (e.g., wherein the distance between individual microneedles varies in no recognizable repeating fashion).

The array can also include other layers attached to the base of the array (i.e., on the side of the array opposite to the microneedle tips). For instance, in some embodiments, the array can further include a protective backing layer to protect the other array components from moisture or other external contaminants as well as mechanical injury, such as from scratching. In some embodiments, the protective backing layer comprises a water-resistant or water-proof plastic film. In some embodiments, the array can include an adhesive backing layer (e.g., so that the array can be attached to another material or to a subject being treated) or a tinted layer (e.g., tinted with a color selected to match a human skin or hair color so that the array can blend better with the skin or hair color of the subject being treated with a patch comprising the array). In some embodiments, the array can include a removable backing layer.

In some embodiments, the presently disclosed subject matter provides a skin patch comprising the microneedle array of the presently disclosed subject matter. In some embodiments, the skin patch can comprise one or more backing layers (e.g., to protect the microneedle array from moisture or other contaminants or physical insult (e.g., scratches). Thus, in some embodiments a water-resistant or water-proof plastic film can be attached to the base layer of the array. In some embodiments, the microneedle array can comprise a layer that extends outward from the array (e.g., coplanar to the base of the array) that comprises a skin-compatible adhesive for aiding in the attachment of the array to the skin. In some embodiments, the patch can further include a decorative or tinted backing layer (e.g., to make the patch less noticeable when attached to the skin surface of a subject being treated with the patch). In some embodiments, the patch includes a removable backing layer (e.g., to make the array less noticeable after the microneedles are embedded in the skin).

In some embodiments, the presently disclosed subject matter provides a method of treating hair loss and/or promoting hair growth in a subject in need thereof, using a microneedle array and/or skin patch of the presently disclosed subject matter. In some embodiments, the method comprises contacting a portion of the skin surface of the subject (e.g., a portion of the skin surface comprising one or more hair follicles and/or a site where hair growth is desired) with a microneedle array or skin patch of the presently disclosed subject matter.

In some embodiments, the array can be contacted to the site for sustained delivery of the combination of the vesicles (e.g., exosomes) and the small molecule hair growth agent for a period of time ranging from about 15 minutes to one or more days (e.g., 1, 2, 3, 4, 5, 6, 7, 8, 9, 10 or more days). In some embodiments, the skin patch can be worn for a period of time ranging from 15 minutes to one or more hours (e.g., 1, 2, 3, 4, 5, 6, 7, or 8 hours) on a daily basis, e.g., until a desired level of new hair growth is observed.

In some embodiments, the subject treated according to the presently disclosed subject matter is a human subject, although it is to be understood that the methods described herein are effective with respect to all mammals.

More particularly, provided herein is the treatment of mammals, such as humans, as well as those mammals of importance due to being endangered (such as Siberian tigers), of economic importance (animals raised on farms for consumption or another use (e.g., the production of wool) by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock and pets.

In some embodiments, the presently disclosed subject matter provides a method of preparing a microneedle array comprising a plurality of microneedles comprising a combination of hair growth agents (e.g., exosomes and a small molecule). In some embodiments, the method comprises providing a mold comprising one or more microneedle (MN)-shaped microcavities. The microcavities can be approximately conical in shape. In some embodiments, the microcavities have a depth of between about 400 and about 1000 micrometers. In some embodiments, the mold comprises silicone.

In some embodiments, a MN patch can be prepared via a "one-step" or a "two-step" method. In some embodiments of the "one-step" method, a solution (e.g., a diluted aqueous solution) comprising a non-keratin hydrophilic polymer optionally keratin or a derivative thereof: vesicles (e.g., exosome, such as MSC-derived exosome) or a related natural product, such as a stem cell or a vesicle-derived protein or nucleic acid; a small molecule growth agent (e.g., nanoparticles comprising the small molecule growth agent); a suitable crosslinking agent; and, optionally a photoinitiator for the crosslinking reaction, can be deposited into the mold comprising MN-shaped cavities. The mold can then be allowed to dry (e.g., at room temperature under vacuum in a vacuum desiccator). If desired, additional amounts of the solution can be added to the mold and/or the mold can be centrifuged to more fully fill the microcavities. After the filled mold is dried, the array can be removed from the mold and, depending upon the crosslinking agent used, exposed to UV radiation to crosslink the array.

In some embodiments, in a "two-step" method, the microneedles can be prepared by dropping a first solution (e.g., a diluted aqueous solution) comprising a non-keratin hydrophilic polymer; optionally keratin or a derivative thereof; vesicles (e.g., exosome, such as MSC-derived exosome) or a related natural product, such as a stem cell or a vesicle-derived protein or nucleic acid; a small molecule growth agent (e.g., nanoparticles comprising the small molecule growth agent, e.g., UK5099); a suitable crosslinking agent; and, optionally a photoinitiator, into the mold comprising MN-shaped cavities. The mold can then be maintained (e.g., under vacuum) for a period of time to more fully deposit and/or condense the solution in the cavities. In some embodiments, the mold can be centrifuged to aid in depositing the solution in the microcavities. The dropping, maintaining, and/or centrifuging steps can be repeated as necessary to more fully fill the MN cavities.

Then, a second solution can be dropped onto the mold. In some embodiments, the second solution comprises a crosslinkable biocompatible polymer, such as, but limited to acrylate-modified hyaluronic acid (m-HA), keratin, a suitable crosslinking agent (e.g., N,N'-methylenebis(acrylamide) (MBA), and a photoinitiator (e.g., Irgacure 2959). The mold can then be dried (e.g., in a vacuum desiccator) and removed from the mold. UV radiation can be applied to the mold to crosslink the base layer.

Figure 2A:
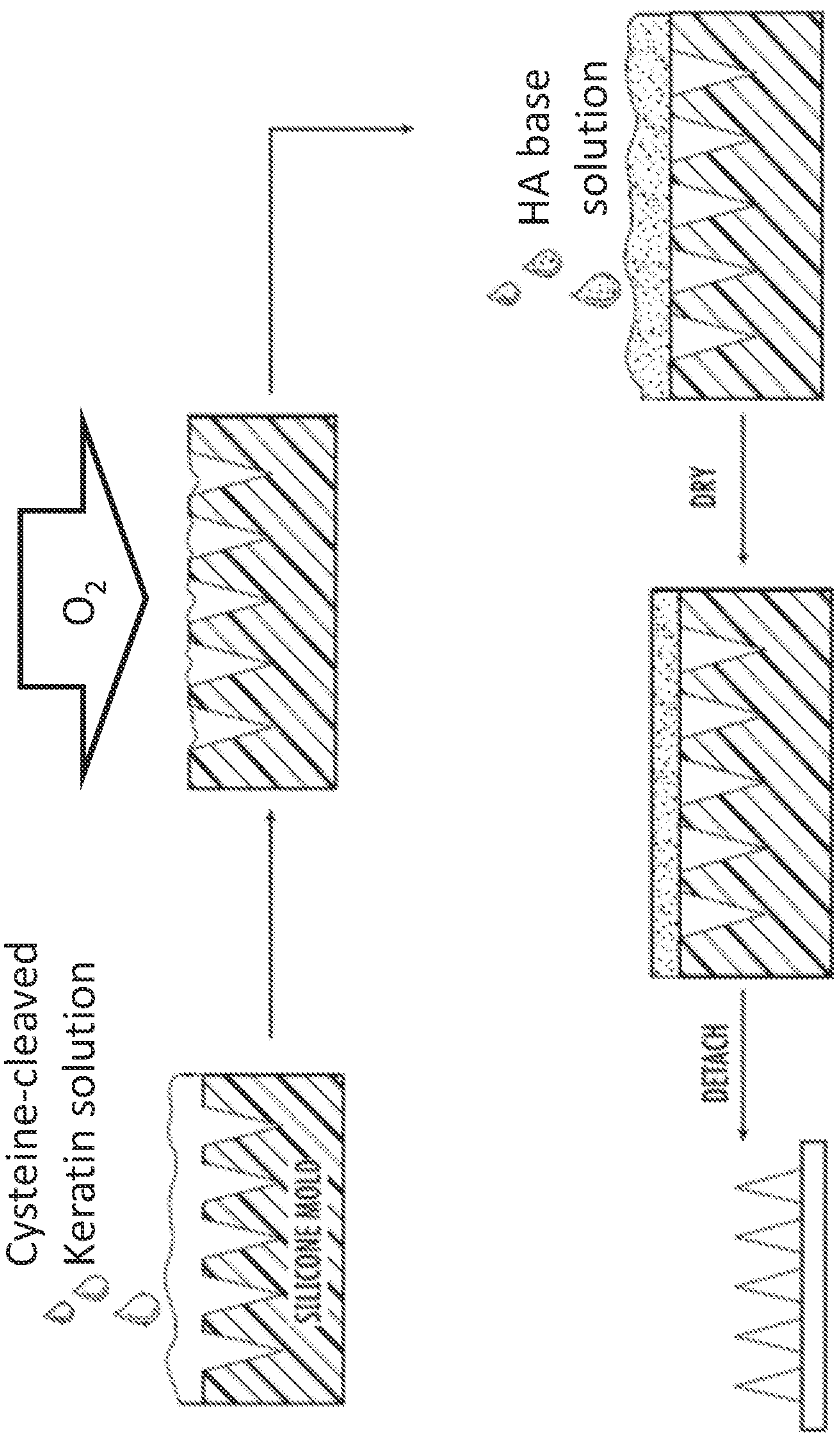
FIG. 2A is a schematic drawing of a process for preparing an exemplary microneedle skin patch of the presently disclosed subject matter for the delivery of hair growth therapeutics using a silicone mold. In the top left, a keratin solution containing cysteine, exosomes, and therapeutic-loaded polymer nanoparticles is deposited in needle cavities. The mold is kept in air (top right) as the keratin hydrogel forms in the microneedle cavities. Then, a solution of hyaluronic acid is added onto the mold (bottom right) and allowed to dry to form the base layer for the microneedle patch (bottom middle). Once dry, the patch is detached from the mold (bottom left).

In some embodiments, such as shown in FIG. 2A, a MN array patch comprising microneedles comprising a keratin hydrogel can be prepared by a method comprising: (a) providing a mold comprising one or more microcavities, optionally wherein each of the one or more microcavities is approximately conical in shape and/or wherein the microcavities have a depth of between about 400 and about 1000 micrometers; (b) filling at least a portion of the one or more microcavities of the mold with a first aqueous solution comprising: (i) keratin, (ii) a natural product, such as a natural product selected from vesicles (e.g., exosomes), stem cells and vesicle-derived molecules (e.g., exosome-derived molecules); (iii) a small molecule hair growth therapeutic agent, and (iv) cysteine; (c) forming a keratin hydrogel in the microcavities for a period of time (e.g., placing the filled mold under air or oxygen for a period of time (e.g., about 30 minutes to about 3 hours, optionally about 1 hour) to form the keratin hydrogel); (d) dropping a second aqueous solution onto the mold (i.e., on top of the keratin hydrogel), wherein said second aqueous solution comprises a hydrophilic polymer; (e) drying the mold for an additional period of time; and (f) removing the microarray from the mold. In some embodiments, the natural produce is exosomes. In some embodiments, the natural product is MSC-derived exosomes. In some embodiments, the small molecule hair loss therapeutic agent is embedded in a biodegradable polymer nanoparticle (e.g., PGLA). In some embodiments, the small molecule hair growth therapeutic agent is UK5099.

In some embodiments, the first aqueous solution comprises between about 5 wt % and about 12 wt % keratin and between about 0.1 wt % cysteine and about 1.0 wt % cysteine. In some embodiments, the first aqueous solution comprises between about 7 wt % and about 9 wt % keratin. In some embodiments, the first aqueous solution comprises about 8 wt % keratin. In some embodiments, the keratin is an extract from human hair. In some embodiments, the first aqueous solution comprises between about 0.25 wt % and about 0.75 wt % cysteine. In some embodiments, the first aqueous solution comprises about 0.4 wt % cysteine.

In some embodiments, steps (b) and (c) are repeated one or more times (e.g., to more completely fill in the microneedle cavities). In some embodiments, an additional aqueous solution (i.e., a third aqueous solution) comprising keratin and cysteine (but without a natural product (e.g., exosomes) or a small molecule hair growth therapeutic agent) is added to the microcavities prior to step (c) to completely fill the microcavities. In some embodiments, excess first aqueous solution (and/or excess additional/third aqueous solution comprising keratin and cysteine) is removed from the mold (e.g., using a plastic scraper or metal blade) prior to step (c) to provide an even/level hydrogel surface at the base of the microneedles. In some embodiments, the second aqueous solution comprises hyaluronic acid.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Preparation of UK5099-Loaded Particles and Microneedle Arrays

Preparation of UK5099-loaded PLGA nanoparticles: UK5099-loaded PLGA nanoparticles were prepared via an emulsion/solvent evaporation method. Briefly, 5 mg PLGA and 0.2 mg 2-cyano-3-(1-phenyl-1H-indol-3-yl)-2-propenoic acid (UK5099), a commercially available small molecule hair follicle stem cell activator, were dissolved in 0.4 ml dichloromethane (DCM), followed by 1 ml of 3% poly(vinyl alcohol (PVA) solution. After sonication, the mixture was dispersed into 4 ml 0.3% PVA solution under stirring and the DCM was removed in a rotary evaporator. The morphology and size of the resultant nanoparticles were characterized by transmission electron microscopy (TEM) and dynamic light scattering (DLS) analysis. The quantitative analysis of UK5099 was performed by high performance liquid chromatography (HPLC).

Isolation and purification of munne exosomes from MSCs: MSCs were derived from mouse bone marrow and cultured in Dulbecco's Modified Eagle Medium, Nutrient Mixture F-12 (DMEM-F12; ThermoFisher Scientific, Waltham, Massachusetts, United States of America) supplemented with 10% extracellular vesicle (EV)-depleted fetal bovine serum (FBS) and 1% penicillin-streptomycin at 37° C. with 5% C02. The MSC-derived exosomes were isolated from MSCs according to a previously published procedure. See Raiendran et al. (2017) Scientific Reports, 7, 15560. For quantitative analysis, the exosomes were labeled with 1,1'-Dioctadecyl-3,3,3',3'-tetramethyl-indocarbacyanine perchlorate (DiI) molecular probes.

Preparation and characterization of human MSC-derived exosomes: Human bone marrow mesenchymal stem cells (MSCs) were cultured using the HyClone AdvanceSTEM mesenchymal stem cell expansion kit (GE Healthcare Life Sciences, Chicago, Illinois, United States of America). When MSCs grew to 70% confluence, the cells were cultured in mesenchymal stem cell basal medium supplemented with 10% EV-depleted fetal bovine serum at 37° C. with 5% CO2 for two days. MSC-derived exosomes were isolated from the cell culture media using the INVITROGEN$^{T}$m total exosome isolation reagent (Life Technologies Corporation, Carlsbad, California, United States of America) according to the protocol. The purified exosomes were observed by transmission electron microscopy. The DiI-labeled exosomes were prepared using a lipophilic tracer, DiI fluorescent dye (ThermoFisher Scientific, Waltham, Massachusetts, United States of America), according to the manufacturer's protocol for quantitative analysis and fluorescent imaging.

Extraction of keratin from human hair: Undyed human hair was collected from a local hair salon, thoroughly washed with water, and defatted with acetone by Soxhlet extraction. The chemically reductive extraction of keratin was performed according to previous work (see Yana et al., Mater. Sci. Eng. C 2018, 83, 1-8) with a few modifications. Briefly, the defatted hair was immersed in a reaction solution containing 8 moles per liter (mol/l) urea, 0.5 mol/l $Na_2S_2O_5$, and 0.2 mol/l sodium dodecyl sulfate (SDS) at 80° C. for 10 h. Then, the mixture was filtered to remove unreacted hair, and the filtrate was dialyzed against deionized water using a cellulose membrane (MWCO=4500 Da) for 48 h. Finally, the dialysate was lyophilized into powder for further use. The contents of free thiol groups and total thiol groups of the regenerated keratin were determined by Ellman's assay according to the literature. See Chan and Wasserman, Cereal Chem. 1993, 70, 22-26.

Preparation of microneedle (MN) patch comprising non-keratin polymer network/keratin microneedles: The preparation of a MN patch was performed using a uniform silicone mold with each needle having a round base diameter of 300 μm and a height of 800 μm using a method similar to previously published procedures. See Zhang et al., (2017) ACS Nano, 11, 9223-9230.

For the "two-step" method: 1 ml of a m-HA/keratin solution (w/v: 1-3%, mass ratio of m-HA/keratin=2/1) containing 200 μg DiD-labeled exosomes, 3.4 μg of UK5099-loaded PLGA nanoparticles, N,N'-methylenebis(acrylamide) (MBA, 1-20% w/w of m-HA) and photoinitiator (irgacure 2959, 1-5% w/w of m-HA) was first deposited onto the mold surface, followed by treatment under vacuum for 6 hours. Then, 3 ml of HA solution (m/v: 4%) was added into the prepared micromold reservoir and allowed to dry at room temperature under vacuum in a vacuum desiccator.

For the "one-step" method: 4 ml of a m-HA/keratin solution (w/v: 2-4%, mass ratio of m-HA/keratin=2/1) containing 100 μg-2 mg exosomes, 2 μg-1 mg of UK5099-loaded PLGA nanoparticles, N,N'-methylenebis(acrylamide) (MBA, 1-20% w/w of m-HA), and photoinitiator (irgacure 2959, 1-5% w/w of m-HA) was deposited onto the mold surface, and allowed to dry at room temperature under vacuum in a vacuum desiccator.

After complete desiccation, the MN patch was detached from the silicone mold. The morphology of the MNs was characterized by scanning electron microscope (SEM).

Preparation of exosomes- and/or UK5099-loaded keratin hydrogel MN (HMN) patch: The fabrication of a "HMN" patch was performed using the silicone micromold with each needle cavity of 300 μm in round base diameter and 600 μm in height. These needle cavities are arranged in a 15×15 array with 600 μm tip-tip spacing. For the preparation of HMN patch, first, 50 μl of 8 wt % keratin solution containing 0.4 wt % cysteine, 200 μg exosomes, and 3.4 μg UK5099-loaded PLGA NPs (about 0.17 μg UK5099) was deposited into the needle cavities and kept under vacuum for 30 minutes. Then, another 50 μl of 8 wt % keratin solution containing 0.4 wt % cysteine was deposited to fill the needle cavities, followed by removal of the excessive keratin solution via a plastic scraper. This silicone micromold was kept under air for 1 hour to form a keratin hydrogel. Subsequently, 1 ml of hyaluronic acid (HA) solution (4 wt % in $H_2O$, Mw=3000 kDa) was loaded onto the micromold and allowed to dry at room temperature. After complete desiccation, the HMN patch was detached from the silicone mold for further use. For the preparation of a "PMN" patch, no cysteine was added in the keratin solution.

Discussion: Fabrication of a stable keratin hydrogel structure was first studied. Gelation of keratin was performed using a keratin concentration of least 15% keratin; however, an increase of the protein concentration to above 20% results in a tough fabrication process due to high viscosity of solution and a long gelation time (>10 hours). It was determined that the amount of disulfide bonds in keratins was about 426 μmol/g protein. Based on this finding, a disulfide reshuffling strategy was applied to prepare a keratin-based hydrogel at lower protein concentrations.

Figure 1B:
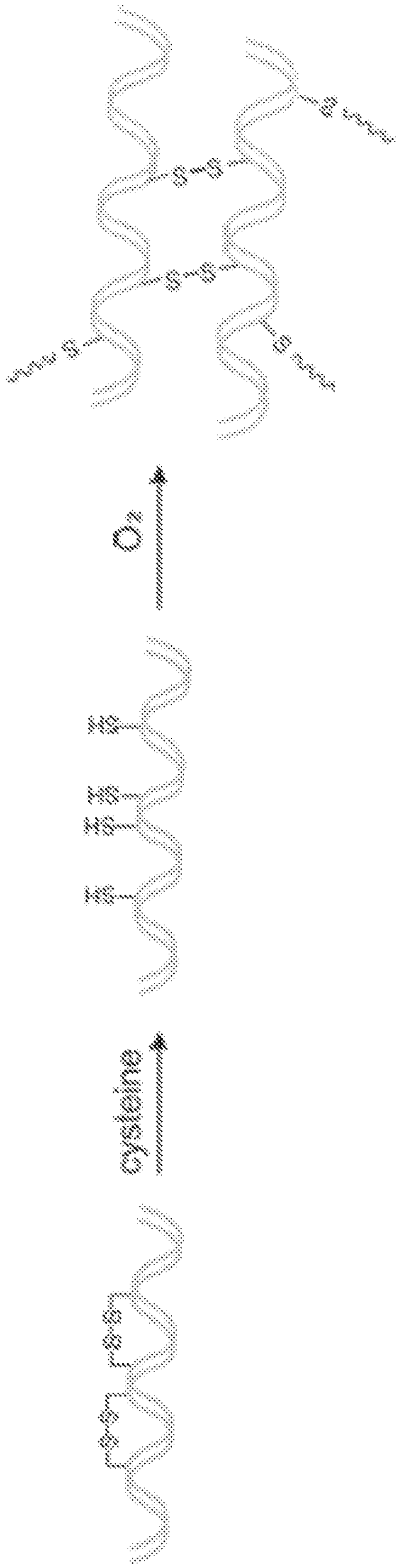
FIG. 1B is a schematic drawing showing the formation of a keratin hydrogel. In a first step (left), the intramolecular disulfide bonds in keratin are cleaved by cysteine to form free thiols, which then form intermolecular disulfide bonds through thiol oxidation (right).

According to this strategy, cysteine was used as a biocompatible reagent to cleave the intramolecular disulfide bonds in the keratin. This strategy provides for the gelation of keratin in a short gelation time due to the thiol oxidation reaction instead of time-consuming physical interactions. See Singh et al., Thiol-Disulfide Interchange, John Wiley & Sons, Inc., Chichester, United Kingdom, 1993, 6433-658. More particularly, according to the disulfide reshuffling strategy, the inherent intramolecular disulfide bonds in keratin were first cleaved by the reductive reagent to generate free thiol groups, which could be re-crosslinked by oxidation to form intermolecular disulfide bonds. See FIG. 1B. By this way, a stable keratin hydrogel with a protein concentration of about 8 wt % was formed within less than 1 hour by introducing about 0.4 wt % cysteine (the molar ratio of cysteine/disulfide bonds was about 1/1). Moreover, this strategy maintained the natural keratin structure, as observed by comparison of the FTIR spectra of keratin powder and the present hydrogel, as it was free of extra chemical modification or external crosslinkers.

Figure 2B:
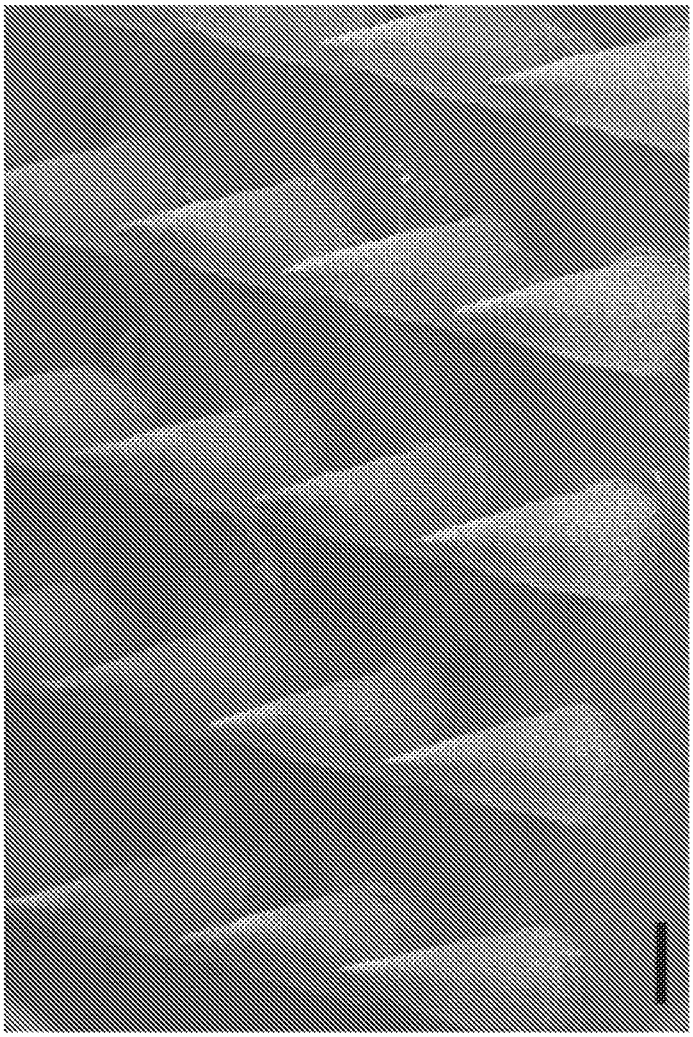
FIG. 2B is a scanning electron microscopy (SEM) image of an exemplary microneedle (MN) array of the presently disclosed subject matter. The scale bar in the lower left of the image represents 200 microns (μm). The MNs comprise a polymeric network of a crosslinked hydrophilic polymer, keratin, exosomes, and small molecule therapeutic-loaded polymer nanoparticles.

A simple two-step procedure was explored to prepare a detachable hydrogel microneedle patch (designated as HMN). In brief, the keratin hydrogel-based microneedles were first formed, and subsequently covered by a water-soluble hyaluronic acid (HA)-based patch base. See FIG. 2A. The resulting microneedles were arranged in a 15×15 array on a 9×9 mm patch. A combined structure could be identified from a fluorescence image of a representative HMN patch prepared by rhodamine B-labeled keratin and FITC-labeled HA. The SEM images demonstrated that each microneedle was conical with a base diameter of 300 μm and a height of 600 μm, coupled with an intact and uniform morphology. See FIG. 2B. For comparison, the traditional gelation method with no addition of cysteine was also performed to prepare microneedles (designated as PMN). In contrast to the HMN patch, in the PMN patch, an interfusion of HA with keratin was observed in the microneedle region, as well as a cracked and uneven morphology. The structure differences between the HMN and PMN patch also exerted influences in the mechanical strength of the microneedles. The HMN patch exhibited a much higher failure force of 2.9 N per needle compared to that of the PMN patch, which had a failure force of 1.7 N per needle, ensuring a sufficient stiffness for skin insertion

Example 2

In Vitro Studies

Loading amount of exosomes and UK5099 in microneedles: The loading amount of cargos in the microneedles was defined as the difference between the cargo loading in the whole HMN patch and that in the patch base. The total amount of cargoes added in the preparation of the MN patch was considered as the cargo loading in the whole MN patch. For detection of the loading amount in the patch base, the HMN patch loaded with DiI-labelled exosomes and UK5099-loaded PLGA NPs was first inserted into the mouse skin for 4 h, followed by removal of the patch base. Then, the patch base was immersed into PBS solution. The amounts of exosomes or UK 5099 in the solution were analyze by fluorescence and HPLC, respectively.

In vitro release studies: The in vitro release profile of DiI-labeled exosomes or UK5099 from the MN, HMN, or PMN patch was determined by immersing the needle tips into the PBS solution at 37° C. At a predetermined time point, the PBS solution was collected and the same volume of fresh PBS solution was added. The concentration of DiI-labeled exosomes or UK5099 released from the patch was determined by fluorescence and HPLC, respectively. The released percentage of DiI labeled-exosomes or UK5099 was recorded at each timepoint, by taking the loading amount of DiI labeled-exosomes or UK5099 in the microneedles as 100%.

MTT assay: The human dermal fibroblast cell was used as the model cell for the 3-(4,5-dimethylthiazol-2-yl)-2,5-diphenyltetrazolium bromide (MTT) assay. After being grown to 70% confluence, the cells were incubated in sample solutions at 37° C. with 5% CO2 for 48 h, including PBS, soak solution of empty HMN needle tips in PBS, soak solution of UK5099-loaded HMN in PBS, soak solution of exosome-loaded HMN in PBS, and pure UK5099 or exosome with the same dosage in HMN. The soak solution of HMN system was obtained by immersing it in PBS for 50 hours.

Statistical Analysis: Data were presented as mean±s.d. Statistics were performed using Student's t test and ANOVA (Prism5 GraphPad).

Figure 3A:
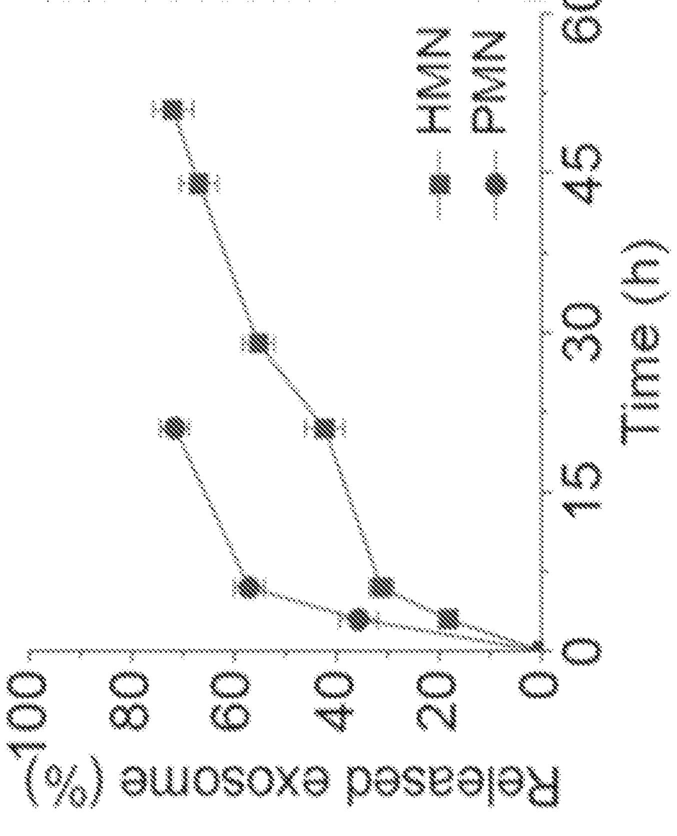
FIG. 3A is a graph showing the accumulated release of dye-labeled exosomes from a microneedle patch of the presently disclosed subject matter in phosphate buffered saline (PBS) at 37 degrees Celsius (° C.) over time (0 to 60 hours (h)). Exosome release is expressed as a percentage (%) of the exosomes initially present in the patch. Data for a patch comprising a keratin WO2019/200063 PCT/US2019/026933 hydrogel prepared using cysteine to break intramolecular disulfide bonds (HMN) is shown in the filled squares, while data for a patch prepared in the absence of cysteine (PMN) is shown in filled circles.
Figure 3B:
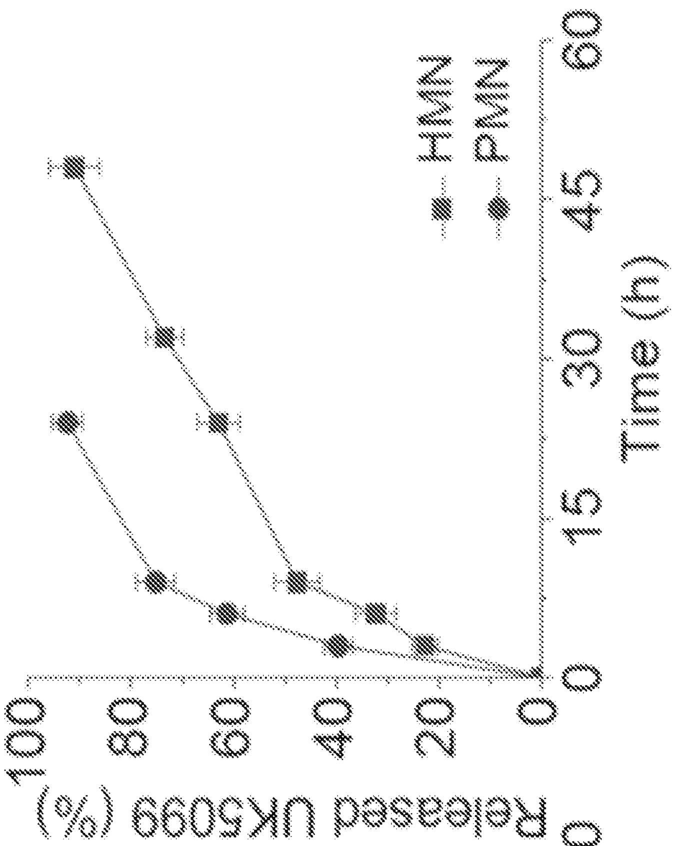
FIG. 3B is a graph showing the accumulated release of 2-cyano-3-(1-phenyl-1H-indol-3-yl)-2-propenoic acid (UK5099) from a microneedle patch of the presently disclosed subject matter in phosphate buffered saline (PBS) at 37 degrees Celsius (° C.) over time (0 to 60 hours (h)). UK5099 release is expressed as a percentage (%) of the UK5099 initially present in the patch. Data for a patch comprising a keratin hydrogel prepared using cysteine to break intramolecular disulfide bonds (HMN) is shown in the filled squares, while data for a patch prepared in the absence of cysteine (PMN) is shown in filled circles.

Discussion: Extracellular vesicle, exosomes and a small molecule, UK5099, were utilized as HFSC activators. Exosomes were isolated from the culture medium of human bone marrow MSCs, showing an average diameter of about 95 nm. To achieve a sustained release effect, UK5099-loaded PLGA nanoparticles (NPs) were prepared and showed an average diameter of about 105 nm. From fluorescence images and digital photographs of a representative HMN patch that contained the DiI-labeled exosomes and UK5099-loaded PLGA NPs, it was observed that the encapsulated cargoes were uniformly distributed inside the microneedles. The loading capacities of exosomes and UK5099 were determined to be 195 μg and 0.16 μg, respectively, in the microneedles, covering 97% and 93%, respectively of the loading amount in the whole HMN patch. FIG. 3A shows the in vitro exosome release profile from the HMN patch, with the PMN patch as a comparison. A sustained and slow release of exosomes was achieved through the HMN patch. Similar phenomenon was found in the release profile of small molecular drug. See FIG. 3B. Gradual release of the embedded DiI-labeled exosomes and UK5099 from MN patches prepared using mixtures of m-HA and keratin was also observed. The release profiles from these patches was similar to that of the HMN patch.

Figure 4:
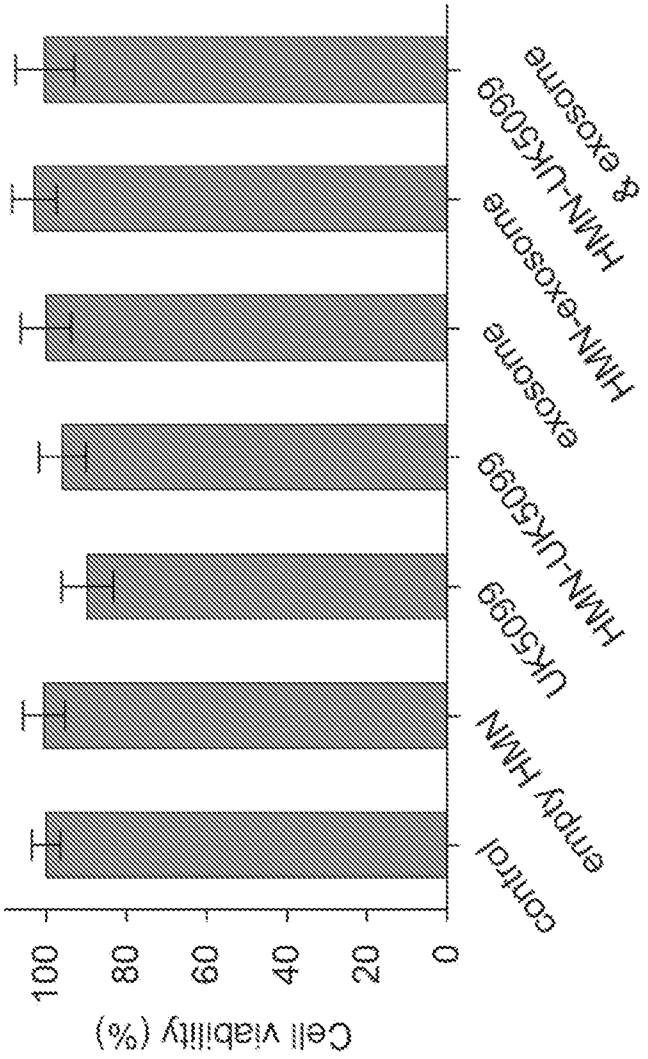
FIG. 4 is a graph showing the in vitro toxicity (as indicated by cell viability as a percentage (%) of cell viability of control) of different treatments of promoting hair growth. Cells were incubated with control (phosphate buffered saline (PBS)), or soak solutions of empty keratin hydrogen microneedle arrays (empty HMN), 2-cyano-3-(1-phenyl-1H-indol-3-yl)-2-propenoic acid (UK5099)-loaded keratin hydrogel microneedle arrays (HMN-UK5099), exosome-loaded keratin hydrogel microneedle arrays (HMN-exosome), or UK5099- and exosome-loaded keratin hydrogel microneedle arrays (HMN-UK5099 & exosomes). For comparison, data for cells treated with pure UK5099 (UK5099) or exosomes (exosome) is also shown.

To evaluate the biocompatibility of the exosomes and UK5099-loaded HMN system, the cytotoxicity of the soak solution of microneedles in PBS was assessed toward the human dermal fibroblast cell. The soak solutions derived from empty microneedles, UK5099-loaded microneedles, exosomes-loaded microneedles, as well as the pure exosomes and UK5099 were investigated as comparison. It was demonstrated that keratin could facilitate cell proliferation by comparing the cell viabilities between the empty HMN and PBS control, as well as between UK5099 or the exosomes-loaded HMN patch and the corresponding pure cargoes. See FIG. 4.

Example 3

In Vivo Studies

Animal Studies: C57B/6J mice were used in this work and purchased from Jackson Laboratory (Bar Harbor, Maine, United States of America). For in vivo therapy studies, the mice were shaved at postnatal day 50, and treated with an HMN patch loaded with exosomes and/or UK5099 at day 1 and day 5 after hair shave. The patch was pressed firmly for the first 5 seconds to penetrate through the epidermis and then pressed softly for an additional 1 minute to make the patch absorb liquid. The patch base was removed at 4 hours post-insertion into the skin. Topical administration of UK5099 (solvent formulation: ethanol/water/propylene glycol=5/3/2), and subcutaneous injection of exosomes were performed every two days, with the dosage same with that of the corresponding HMN patch. Shaved mice without any treatment were adopted as a control. The clinical agent minoxidil was used via topical administration in a concentration of 3%. The time profile of the hair phenotype transformation was obtained by real-time observation of the hair regrowth in mice. The judgement of the hair follicles in telogen, telogen-anagen transition, and anagen was performed according to a method previously described in the literature. See Oh et al., J. Investig. Dermatol. 2016, 136(1), 34-44. Hair pull test by tape assay was performed by affixing a tape to the hair coat, then peeling off to assess the amount of hair sticking on the tape.

Statistical Analysis: Data were presented as mean±s.d. Statistics were performed using Student's t test and ANOVA (Prism5 GraphPad). Significant differences between the two groups are noted by asterisks (*P<0.05; P<0.01; *P<0.001).

Western blot: Mice skins were ground and lysed with protease and phosphatase inhibitors. Equal amounts of proteins were separated on SDS-polyacrylamide gel electrophoresis and transferred to a PROTRAN™ nitrocellulose membrane (GE Healthcare Life Sciences, Chicago, Illinois, United States of America). The membrane was blocked with 3% nonfat dry milk for 1 hour and incubated overnight at 4° C. with primary antibodies targeting β-catenin, PCNA, K15, CD34, and ALP, respectively. Antibody to mouse β-actin was used as a control. All the antibodies were purchased from Santa Cruz Biotechnology (Dallas, Texas, United States of America) and diluted at 1:500 in 1.5% bovine serum albumin (BSA) solution. The membranes were washed three times and incubated with horseradish peroxidase-conjugated anti-mouse IgG secondary antibodies (1:2000; Seracare Life Sciences Inc., Milford, Massachusetts, United States of America) for 1 hour at room temperature.

Histology andimmunostaining: For histopathology, the harvested skins were fixed in 10% formalin and paraffin-embedded, sectioned and stained with hematoxylin and eosin. Histopathology images were acquired on EVOS FL fluorescence microscopy (ThermoFisher Scientific, Waltham, Massachusetts, United States of America). For immunostaining, the harvested skins were embedded in OCT, frozen, and cryosectioned (15 μm). All sections for staining were fixed in 4% paraformaldehyde for 10 min, permeabilized in PBST (PBS+0.3% Triton), and blocked in FBS for another 10 min. Then, the sections were incubated overnight at 4° C. with primary antibodies targeting CD3 (Rat, 1:100; eBiosciences Inc., Affymetrix, Santa Clara, California, United States of America) and CD68 (Rat, 1:100; BioLegend, San Diego, California, United States of America). After incubation, the sections were rinsed with PBST and incubated with 1:200 diluted Rhodamine-conjugated IgG secondary antibody at room temperature for 90 min and counterstained with DAPI for 5 min. The fluorescent signals were visualized using EVOS FL fluorescence microscopy (ThermoFisher Scientific, Waltham, Massachusetts, United States of America).

Discussion: The HMN patch could be easily inserted into the mouse skin. An array of micropores could be observed on the skin after removal of the HMN patch at 5 minutes post-insertion, with a depth of about 200 μm. Meanwhile, the patch base could detach from the microneedles at 4 hours post-insertion, leaving the microneedles settled in the skin. See FIG. 1A. In this manner, the HMN system could obtain an invisible appearance on the skin during therapy. Moreover, the HMN system could be biodegraded in vivo within 7-10 days after penetration into skin and removal of the patch base, as evidenced biofluorescence imaging. A significantly longer degradation duration of the HMN system was achieved due to the hydrogel structure of the microneedles in the HMN patch in comparison to the hydrogel structure in the PMN patch.

The biofluorescence images of exosomes-loaded HMN patch treated mice verified a sustained and slow release of exosomes in vivo for a duration of more than 10 days. By contrast, it lasted approximately 7 and 4 days for the exosomes administrated via the PMN patch and subcutaneous injection, respectively.

The histology evaluation of the treated skin was performed by H&E staining, and immunofluorescence staining of mononuclear inflammatory cells at day 5 and 9 post-penetration of the HMN system, with the untreated mouse skin as a control. Negligible inflammation cells were found in the treated skin region by H&E staining. No lymphocyte infiltration (CD3) and negligible macrophage invasion (CD68) were detected in the treated skin, indicating good biocompatibility of the HMN system.

Figure 5A:
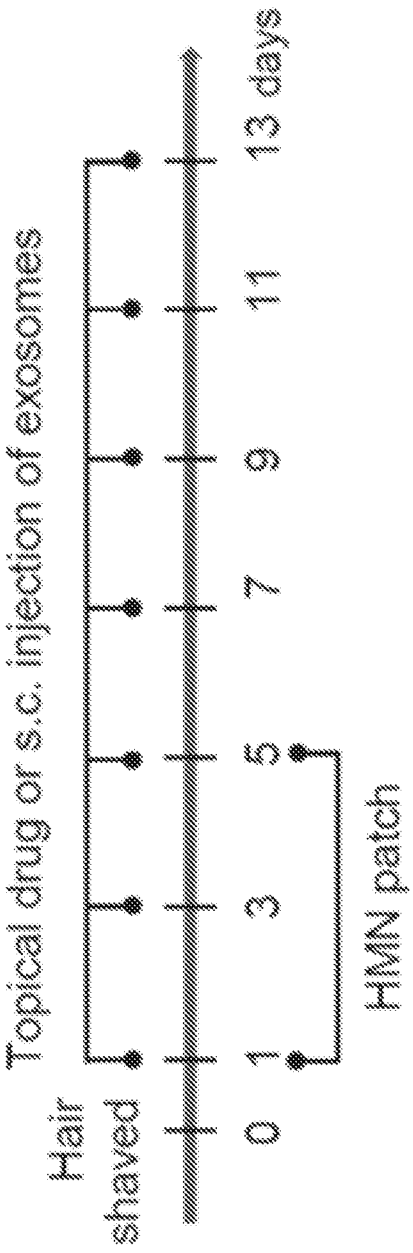
FIG. 5A is a schematic drawing of a hair loss therapy treatment schedule in a mouse model of hair loss via hydrogel microneedle patch administration, topical small molecule administration, or subcutaneous injection (s.c.) treatment.
Figure 5B:
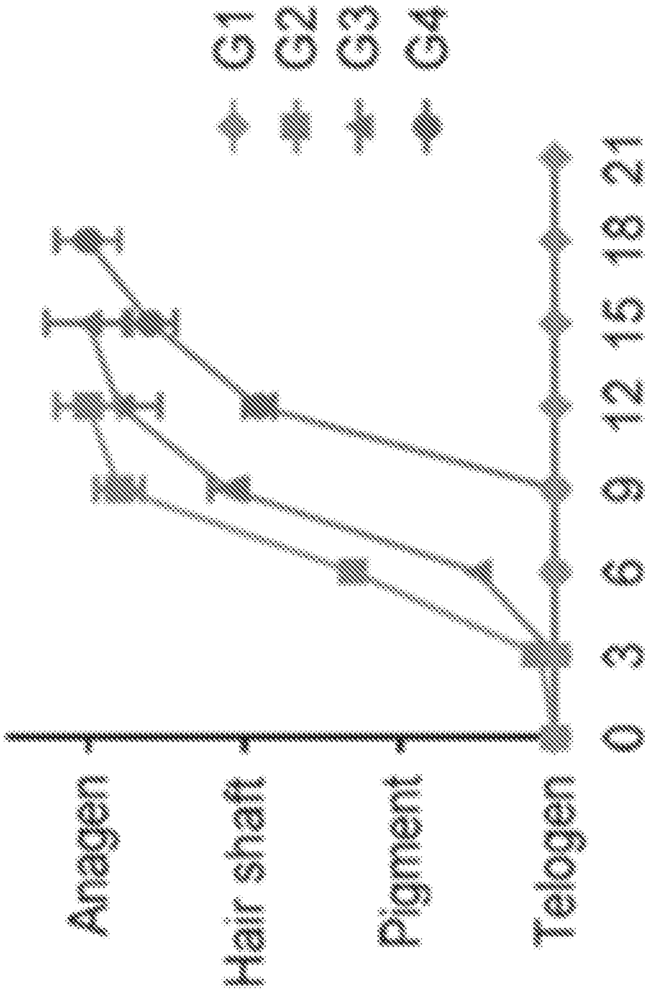
FIG. 5B is a graph showing the time profiles of hair phenotype transformation in mice treated with exosome- and 2-cyano-3-(1-phenyl-1H-indol-3-yl)-2-propenoic acid (UK5099)-loaded keratin hydrogel microneedle arrays (G2; squares), UK5099-loaded keratin hydrogel microneedle arrays (G3, triangles), or exosomes-loaded keratin hydrogel microneedle arrays (G4, circles). For comparison, data is also shown for untreated mice (G1, diamonds). Hair growth stage is indicated on the left axis, while treatment day (corresponding to the schedule shown in FIG. 5A) is indicated on the bottom axis.
Figure 5C:
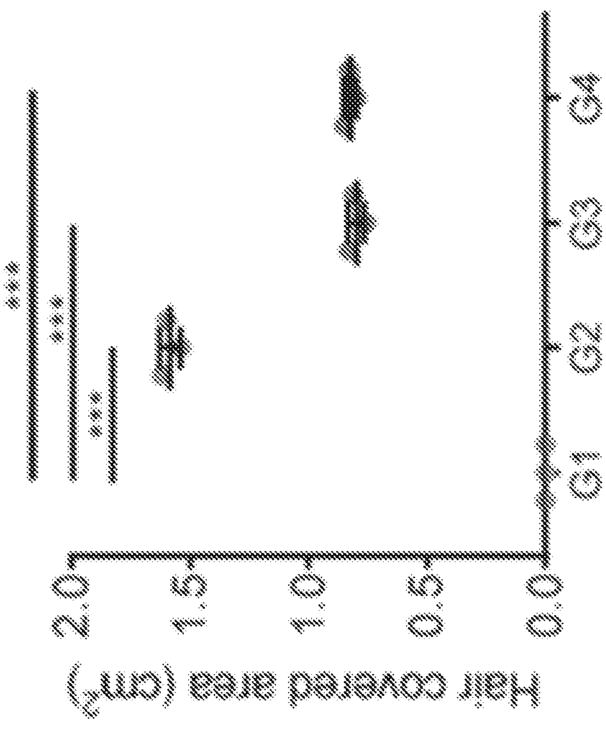
FIG. 5C is a graph showing the hair covered area (in square centimeters ($cm^2$)) of mice treated with exosome- and 2-cyano-3-(1-phenyl-1H-indol-3-yl)-2-propenoic acid (UK5099)-loaded keratin hydrogel microneedle arrays (G2), UK5099-loaded keratin hydrogel microneedle arrays (G3), or exosomes-loaded keratin hydrogel microneedle arrays (G4). For comparison, data is also shown for untreated mice (G1). ***$P<0.001$.
Figure 5D:
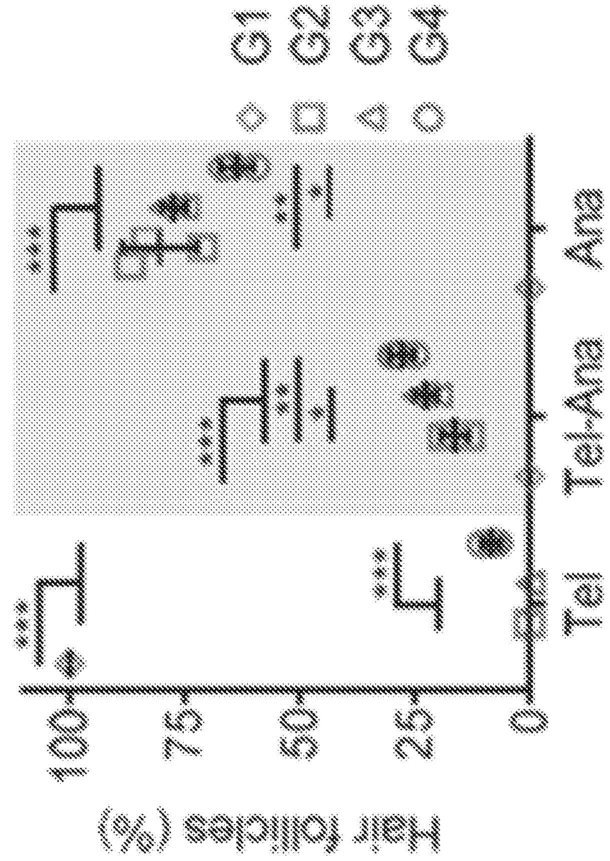
FIG. 5D is a graph showing the quantification of hair follicles (as a percentage (%)) in telogen, telogen-anagen transition and anagen in mice treated with exosome- and 2-cyano-3-(1-phenyl-1H-indol-3-yl)-2-propenoic acid (UK5099)-loaded keratin hydrogel microneedle arrays (G2, squares), UK5099-loaded keratin hydrogel microneedle arrays (G3, triangles), or exosomes-loaded keratin hydrogel microneedle arrays (G4, circles). For comparison, data is also shown for untreated mice (G1, diamonds). *$P<0.05$, $P<0.01$, *$P<0.001$.
Figure 5F:
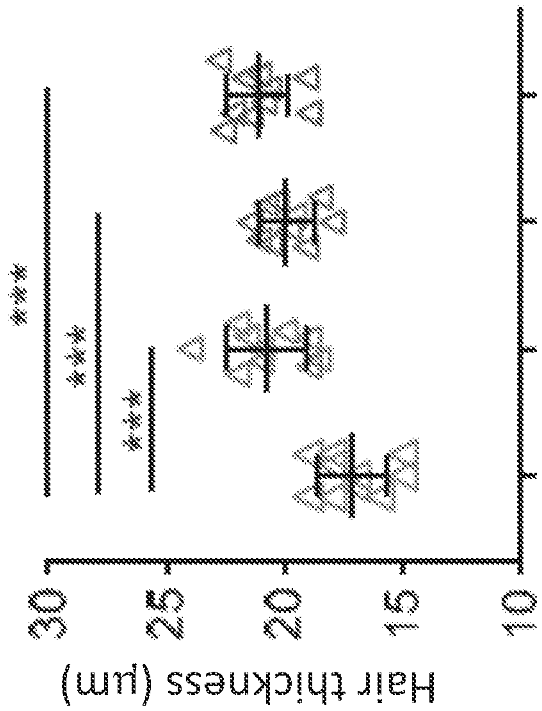
FIG. 5F is a graph showing hair thickness (in micrometers (μm)) of mice treated with exosome- and 2-cyano-3-(1-phenyl-1H-indol-3-yl)-2-propenoic acid (UK5099)-loaded keratin hydrogel microneedle arrays (G2), UK5099-loaded keratin hydrogel microneedle arrays (G3), or exosomes-loaded keratin hydrogel microneedle arrays (G4). For comparison, data is also shown for untreated mice (G1). ***$P<0.001$.
Figure 5E:
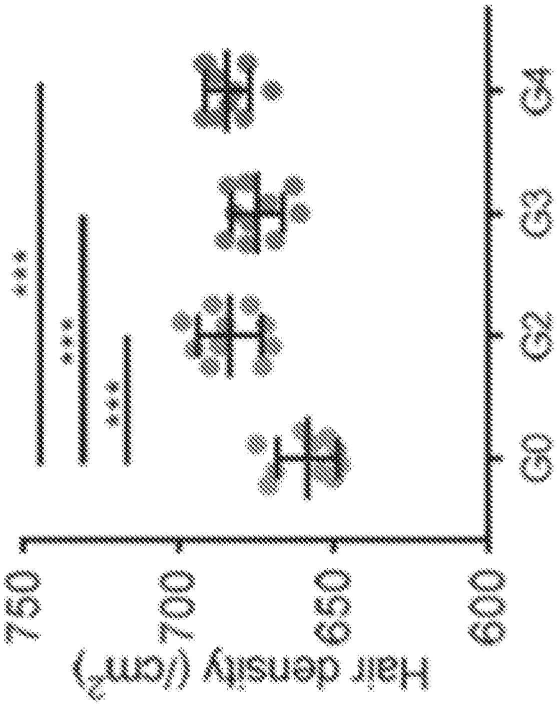
FIG. 5E is a graph showing hair density (hairs per square centimeter ($cm^2$)) of mice treated with exosome- and 2-cyano-3-(1-phenyl-1H-indol-3-yl)-2-propenoic acid (UK5099)-loaded keratin hydrogel microneedle arrays (G2), UK5099-loaded keratin hydrogel microneedle arrays (G3), or exosomes-loaded keratin hydrogel microneedle arrays (G4). For comparison, data is also shown for untreated mice (G1). ***$P<0.001$.

FIG. 5A illustrates the hair loss therapy treatment schedule in a 7-week-old shaved C57BL/6J mouse model by either the HMN patch application, topical administration, or subcutaneous injection administration. The same dosage of exosomes or UK5099 was used in all three treatments. In a sharp contrast, regardless of exosomes or UK5099, the treatment via HMN administration initiated a fast onset of hair regrowth in the treated region by only two rounds of administration, while the conventional tropical drugs, including UK5099 and clinically-used minoxidil, or subcutaneous injection of exosomes generated an inferior therapeutic effect, reflected by the hair covered area even with seven treatments. See FIG. 5C. No obvious hair regrowth was found in the mouse without any treatment or with empty HMN treatment. It was also substantiated that an enlarged area of hair regrowth could be obtained by applying several HMN patches, confirming that the HMN system was an efficient transdermal delivery device for hair regrowth promotion. Moreover, combination treatment allowed HFSCs to enter into anagen within as few as 6 days, indicated by pigmentation and hair regrowth. In comparison, monotherapy by either UK5099 or exosomes exhibited the same effect after about 8 and 11 days of treatment, respectively. See FIG. 5B. The hair regrowth promotion by the HMN system was further confirmed by histomorphometrical analysis of the hair follicles. Compared with the topical or subcutaneous injection administration, the HMN system enabled the hair follicles an apparent entry into anagen, revealed by an elongated morphology extending into the adipose layer with a higher density. See ȟ et al., J. Investig. Dermatol. 2016, 136(1), 34-44; and MuÈller-RoÈver et al., J. Investig. Dermatol., 2001, 117 (1), 3-15. Among the different treatments, the HMN system loaded with both exosomes and UK 5099 achieved the most effective promotion of hair cycle activation, evidenced by the quantification analysis of the hair cycle. See FIG. 5D. Moreover, mice treated by any of the HMN systems obtained a higher hair density and hair thickness than wide-type mice. See FIGS. 5E and 5F. The hair pull test demonstrated that the regrown hair by the HMN system could not be easily peeled off by tape, similar to hair of the wide-type mice. Western blot shows that mice treated by the HMN system got a strong increase in the hair cycle activation-associated protein expression including, β-catenin, K15, CD34, ALP, and PCNA at 10-day post-treatment, consistent with their accelerated entry into a new hair cycle.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A microneedle comprising a composition comprising:

(a) a hydrophilic polymer network comprising a keratin hydrogel with a protein concentration of about 8%, wherein the keratin hydrogel is crosslinked via intermolecular disulfide bonds, wherein the keratin hydrogel is a hydrogel prepared from an aqueous solution comprising between about 5 weight-% (wt %) and about 20 wt % keratin and between about 0.1 wt % and about 1.0 wt % cysteine;

(b) a natural product, wherein the natural product comprises exosomes; and (c) a small molecule hair growth agent, wherein the small molecule hair growth agent is 2-cyano-3-(1-phenyl-1H-indol-3-yl)-2-propenoic acid (UK5099) and wherein a failure force of the microneedle is higher compared to a microneedle comprising a hydrophilic polymer network comprising a keratin hydrogel prepared in the absence of about 0.1 wt % and about 1 wt % cysteine.

2. A microneedle array comprising a plurality of microneedles of claim 1.

3. A skin patch comprising the microneedle array of claim 2, wherein said patch comprises a protective backing layer, a removable backing layer or a backing layer comprising a skin compatible adhesive.

4. A method of treating hair loss and/or promoting hair growth in a subject in need thereof, wherein the method comprises administering the skin patch of claim 3 to the subject, wherein the administering comprises contacting the skin patch with a skin surface of the subject, wherein the skin surface comprises one or more hair follicles.

5. The skin patch of claim 3, wherein the patch is 9×9 mm and comprises a 15×15 array of the plurality of microneedles.

6. A method of treating hair loss and/or promoting hair growth in a subject in need thereof, wherein the method comprises administering the microneedle array of claim 2, wherein the administering comprises contacting the microneedle array with a skin surface of the subject, wherein the skin surface comprises one or more hair follicles.

7. The method of claim 6, wherein the contacting comprises contacting the skin surface of the subject with the microneedle array daily, optionally wherein the daily contacting is for between about one and about 24 hours per day, and wherein the subject is a human.

8. A method of preparing the microneedle array of claim 2, wherein the method comprises: (a) providing a mold comprising one or more microcavities, optionally wherein each of the one or more microcavities is approximately conical in shape and/or wherein the one or more microcavities have a depth of between about 400 and about 1000 micrometers; (b) filling at least a portion of the one or more microcavities of the mold with a first aqueous solution comprising: (i) about 5 weight-% (wt %) and about 20 wt % keratin, (ii) a natural product selected from the group consisting of vesicles, stem cells, and vesicle-derived molecules, optionally wherein the vesicles are exosomes, further optionally wherein the natural product comprises mesenchymal stem cell (MSC)-derived exosomes; (iii) a small molecule hair growth therapeutic agent, and (iv) about 0.1 wt % and about 1.0 wt % cysteine, optionally wherein the molecule hair loss therapeutic agent is embedded in a biodegradable polymer nanoparticle, wherein the small molecule hair growth therapeutic agent is UK5099; (c) placing the mold under air or oxygen for a period of time to form a keratin hydrogel; (d) dropping a second aqueous solution onto the mold, wherein said second aqueous solution comprises a hydrophilic polymer; (e) drying the mold for an additional period of time; and (f) removing the microneedle array from the mold.

9. The method of claim 8, wherein the second aqueous solution comprises hyaluronic acid.

10. The method of claim 8, wherein steps (b) and (c) are repeated one or more times.

11. The microneedle array of claim 2, wherein each of said plurality of microneedles has a length of between about 400 and about 1000 micrometers.

12. The microneedle array of claim 2, wherein each of the plurality of microneedles has a length of about 600 micrometers and a base diameter of about 300 micrometers.

13. The microneedle array of claim 2, wherein the plurality of microneedles are positioned in a 15×15 array.

14. The microneedle of claim 1, wherein the natural product comprises mesenchymal stem cell (MSC)-derived exosomes.

15. The microneedle of claim 1, wherein the keratin hydrogel is a hydrogel prepared from an aqueous solution comprising about 8 weight % keratin and/or about 0.4 wt % cysteine.

16. The microneedle of claim 1, wherein the hydrophilic polymer network comprises: (i) a crosslinked hydrophilic polymer wherein the crosslinked hydrophilic polymer is different than keratin; and (ii) keratin or a derivative thereof.

17. The microneedle of claim 16, wherein the crosslinked hydrophilic polymer is selected from the group consisting of methacrylated hyaluronic acid (m-HA) or another glucosaminoglycan or copolymer or derivative thereof; polyvinyl alcohol (PVA) or a copolymer or derivative thereof; a polysaccharide; a poly(amino acid), a protein other than keratin; polyvinyl pyrrolidone (PVP); a poly(alkylene glycol) or a poly(alkylene oxide); poly(hydroxyalkyl methacrylamide), a polyhydroxy acid; combinations thereof, and copolymers thereof.

18. The microneedle of claim 1, wherein the small molecule hair growth agent is encapsulated in a nanoparticle comprising a biodegradable polymer.

19. The microneedle of claim 18, wherein the biodegradable polymer is polylactic-co-glycolic acid (PLGA).

20. The microneedle of claim 1, wherein the composition comprises between about 0.01 milligrams (mg) and about 2 mg exosomes.

21. The microneedle of claim 1, wherein the composition comprises between about 0.05 micrograms (μg) and about 1 mg of the small molecule hair growth agent.

22. The microneedle of claim 1, wherein the protein concentration of the keratin hydrogel is less than a keratin hydrogel prepared in the absence of about 0.1 wt % and about 1 wt % cysteine.

* * * * *